US008043091B2

(12) United States Patent
Schmitt

(10) Patent No.: US 8,043,091 B2
(45) Date of Patent: Oct. 25, 2011

(54) COMPUTER MACHINED DENTAL TOOTH SYSTEM AND METHOD

(75) Inventor: Stephen M. Schmitt, San Antonio, TX (US)

(73) Assignee: Voxelogix Corporation, San Antonio, TX (US)

( * ) Notice: Subject to any disclaimer, the term of this patent is extended or adjusted under 35 U.S.C. 154(b) by 841 days.

(21) Appl. No.: 11/739,310

(22) Filed: Apr. 24, 2007

(65) Prior Publication Data

US 2007/0190492 A1  Aug. 16, 2007

Related U.S. Application Data

(63) Continuation-in-part of application No. 11/674,956, filed on Feb. 14, 2007.

(60) Provisional application No. 60/794,996, filed on Apr. 26, 2006, provisional application No. 60/773,433, filed on Feb. 15, 2006.

(51) Int. Cl.
 *A61C 9/00* (2006.01)
(52) U.S. Cl. ........................ 433/196; 433/213
(58) Field of Classification Search .................. 433/196, 433/213, 214, 223; 264/17, 19
See application file for complete search history.

(56) References Cited

U.S. PATENT DOCUMENTS

| 4,208,794 A | 6/1980 | Gerber |
| 4,226,592 A | 10/1980 | Schreinemakers |
| 4,575,805 A | 3/1986 | Moermann et al. |
| 4,615,678 A | 10/1986 | Moermann et al. |
| 4,766,704 A | 8/1988 | Brandestini et al. |
| 4,795,345 A | 1/1989 | Ai et al. |
| 4,837,732 A | 6/1989 | Brandestini et al. |
| 4,901,737 A | 2/1990 | Toone |
| 5,006,065 A | 4/1991 | Waysenson |
| 5,409,017 A | 4/1995 | Lowe |
| 5,501,598 A | 3/1996 | Misch |
| 5,527,182 A | 6/1996 | Willoughby |
| 5,605,459 A * | 2/1997 | Kuroda et al. ............... 433/214 |
| 5,652,709 A | 7/1997 | Andersson et al. |
| 5,662,476 A | 9/1997 | Ingber et al. |
| 5,690,843 A | 11/1997 | Schmitt et al. |
| 5,697,997 A | 12/1997 | Aronsson et al. |
| 5,725,378 A | 3/1998 | Wang |

(Continued)

FOREIGN PATENT DOCUMENTS

EP  1561433 A1  8/2005

(Continued)

OTHER PUBLICATIONS

PCTUS07062171, Feb. 2007, Dental Implant Technologies, Inc., International Search Report.

(Continued)

*Primary Examiner* — Ralph Lewis
(74) *Attorney, Agent, or Firm* — Cox Smith Matthews Incorporated

(57) ABSTRACT

A method and system for making a dental prosthetic includes, for example, arranging a first virtual tooth image relative to a second virtual tooth image on a virtual denture set and locating a first actual prosthetic tooth relative to a second actual prosthetic tooth in a manner corresponding to the arranged first and second virtual images. The method also may include performing at least one Boolean operation to remove a portion of the first virtual tooth image and the second virtual tooth image and machining the first actual prosthetic tooth and the second actual prosthetic tooth to remove a portion correspond to material removed by the Boolean operation performed on the first and second virtual tooth images.

10 Claims, 41 Drawing Sheets

U.S. PATENT DOCUMENTS

| | | | |
|---|---|---|---|
| 5,733,126 A | 3/1998 | Andersson et al. | |
| 5,741,215 A | 4/1998 | D'Urso | |
| 5,768,134 A | 6/1998 | Swaelens et al. | |
| 5,779,477 A | 7/1998 | Boss | |
| 5,800,174 A | 9/1998 | Andersson | |
| 5,807,102 A | 9/1998 | Lang et al. | |
| 5,816,810 A | 10/1998 | Antonson et al. | |
| 5,823,778 A | 10/1998 | Schmitt et al. | |
| 5,829,981 A | 11/1998 | Ziegler | |
| 5,851,115 A | 12/1998 | Carlsson et al. | |
| 5,857,853 A | 1/1999 | van Nifterick et al. | |
| 5,868,138 A | 2/1999 | Halstrom | |
| 5,871,358 A | 2/1999 | Ingber et al. | |
| 5,880,962 A | 3/1999 | Andersson et al. | |
| 5,938,446 A | 8/1999 | Andersson et al. | |
| 5,951,289 A | 9/1999 | Kura et al. | |
| 5,967,777 A | 10/1999 | Klein et al. | |
| 5,975,893 A | 11/1999 | Chishti et al. | |
| 5,989,029 A | 11/1999 | Osorio et al. | |
| 5,993,214 A | 11/1999 | Persson | |
| 6,015,289 A | 1/2000 | Andreiko et al. | |
| 6,055,986 A | 5/2000 | Meade | |
| 6,062,860 A | 5/2000 | Jorgenson | |
| 6,066,274 A | 5/2000 | Antonson et al. | |
| 6,082,995 A | 7/2000 | Wise | |
| 6,126,445 A | 10/2000 | Willoughby | |
| 6,149,433 A | 11/2000 | Ziegler et al. | |
| 6,152,731 A | 11/2000 | Jordan et al. | |
| 6,155,828 A | 12/2000 | Lazzara et al. | |
| 6,159,010 A | 12/2000 | Rogers et al. | |
| 6,168,435 B1 | 1/2001 | Beaty et al. | |
| 6,186,790 B1 | 2/2001 | Karmaker et al. | |
| 6,210,162 B1 | 4/2001 | Chishti et al. | |
| 6,217,325 B1 | 4/2001 | Chishti et al. | |
| 6,217,331 B1 | 4/2001 | Rogers et al. | |
| 6,227,851 B1 | 5/2001 | Chishti et al. | |
| 6,231,342 B1 | 5/2001 | Osorio et al. | |
| 6,261,098 B1 | 7/2001 | Persson | |
| 6,276,938 B1 | 8/2001 | Jorneus et al. | |
| 6,283,752 B1 | 9/2001 | Kumar | |
| 6,287,116 B2 | 9/2001 | Lazzara | |
| 6,287,119 B1 | 9/2001 | van Nifterick et al. | |
| 6,302,686 B1 | 10/2001 | Chott et al. | |
| 6,305,939 B1 | 10/2001 | Dawood | |
| 6,319,006 B1 | 11/2001 | Scherer et al. | |
| 6,322,359 B1 | 11/2001 | Jordan et al. | |
| 6,343,930 B1 | 2/2002 | Beaty et al. | |
| 6,354,836 B1 | 3/2002 | Panzera et al. | |
| 6,361,318 B1 | 3/2002 | Back et al. | |
| 6,382,975 B1 | 5/2002 | Poirier | |
| 6,394,801 B2 | 5/2002 | Chishti et al. | |
| 6,409,504 B1 | 6/2002 | Jones et al. | |
| 6,419,489 B1 | 7/2002 | Jorneus et al. | |
| 6,419,491 B1 | 7/2002 | Ricci et al. | |
| 6,431,866 B2 | 8/2002 | Hurson | |
| 6,463,344 B1 | 10/2002 | Pavloskaia et al. | |
| 6,491,723 B1 | 12/2002 | Beaty | |
| 6,505,625 B1 | 1/2003 | Uenishi | |
| 6,524,106 B1 | 2/2003 | Ziegler | |
| 6,530,375 B1 | 3/2003 | Cieslik, Jr. | |
| 6,540,516 B1 | 4/2003 | Ziegler | |
| 6,558,162 B1 | 5/2003 | Porter et al. | |
| 6,582,931 B1 | 6/2003 | Kois et al. | |
| 6,607,386 B1 | 8/2003 | Andersson et al. | |
| 6,621,491 B1 | 9/2003 | Baumrind et al. | |
| 6,633,789 B1 | 10/2003 | Nikolskiy et al. | |
| 6,640,150 B1 | 10/2003 | Persson et al. | |
| 6,648,645 B1 | 11/2003 | MacDougald et al. | |
| 6,652,765 B1 | 11/2003 | Beaty | |
| 6,655,962 B1 | 12/2003 | Kennard | |
| 6,665,570 B2 | 12/2003 | Pavloskaia et al. | |
| 6,671,539 B2 | 12/2003 | Gateno et al. | |
| 6,705,863 B2 | 3/2004 | Phan et al. | |
| 6,726,478 B1 | 4/2004 | Isiderio et al. | |
| 6,767,208 B2 | 7/2004 | Kaza | |
| 6,820,623 B2 | 11/2004 | Cook | |
| 6,886,566 B2 | 5/2005 | Eubank | |
| 6,935,861 B2 | 8/2005 | Lauciello | |
| 6,947,038 B1 | 9/2005 | Anh et al. | |
| 6,948,936 B2 | 9/2005 | Miller et al. | |
| 7,047,978 B2 | 5/2006 | Zuk | |
| 7,080,979 B2 * | 7/2006 | Rubbert et al. | 433/24 |
| 7,153,135 B1 * | 12/2006 | Thomas | 433/213 |
| 7,267,549 B2 * | 9/2007 | Monkmeyer | 433/197 |
| 7,322,824 B2 * | 1/2008 | Schmitt | 433/215 |
| 7,458,812 B2 * | 12/2008 | Sporbert et al. | 433/24 |
| 2003/0065259 A1 | 4/2003 | Gateno et al. | |
| 2004/0152036 A1 | 8/2004 | Abolfathi | |
| 2004/0172150 A1 | 9/2004 | Perot et al. | |
| 2004/0219490 A1 * | 11/2004 | Gartner et al. | 433/218 |
| 2004/0229185 A1 | 11/2004 | Knopp | |
| 2005/0084144 A1 | 4/2005 | Feldman | |
| 2005/0106528 A1 | 5/2005 | Abolfathi et al. | |
| 2005/0136371 A1 | 6/2005 | Abolfathi et al. | |
| 2005/0153257 A1 | 7/2005 | Durbin et al. | |
| 2005/0170311 A1 | 8/2005 | Tardieu et al. | |
| 2005/0214716 A1 * | 9/2005 | Weber et al. | 433/173 |
| 2005/0244791 A1 | 11/2005 | Davis et al. | |
| 2005/0271996 A1 | 12/2005 | Sporbert et al. | |
| 2006/0068355 A1 | 3/2006 | Schultz | |
| 2006/0111806 A1 | 5/2006 | Kraemer et al. | |
| 2006/0263738 A1 | 11/2006 | Kuo | |
| 2007/0031791 A1 | 2/2007 | Cinader, Jr. et al. | |
| 2007/0118243 A1 | 5/2007 | Schroeder et al. | |
| 2007/0134625 A1 | 6/2007 | Leu et al. | |
| 2007/0190481 A1 | 8/2007 | Schmitt | |
| 2008/0020350 A1 | 1/2008 | Matov et al. | |
| 2008/0064008 A1 | 3/2008 | Schmitt | |
| 2008/0085489 A1 | 4/2008 | Schmitt | |

FOREIGN PATENT DOCUMENTS

| | | |
|---|---|---|
| GB | 2440267 A | 1/2008 |
| WO | WO9528688 | 10/1995 |
| WO | WO9932045 | 7/1999 |
| WO | WO2006009747 | 1/2006 |
| WO | 2006031096 A1 | 3/2006 |
| WO | 2006096558 A2 | 9/2006 |
| WO | 2007079142 A2 | 7/2007 |
| WO | 2007084589 A2 | 7/2007 |
| WO | 2007084727 A1 | 7/2007 |
| WO | 2007130574 A1 | 11/2007 |

OTHER PUBLICATIONS

WO2007127804 A3, Feb. 28, 2008, Dental Implant Technologies, Inc., International Search Report.

Schmitt, The 3rd Annual Eugene C. Gwaltney Manufacturing Symposium, "Rapid Prototyping for Product Development, Design, and Tooling: Making the New Technologies Pay Off for You" "Changing Peoples' Lives with RPM",Oct. 1-3, 1996, pp. 75-83 (10 pages).

Schmitt, The 4th Annual Eugene C. Gwaltney Manufacturing Symposium, "Rapid Prototyping and Manufacturing: Application in Product Development, Design and Tooling", "Changing Lives with RP", Georgia Institute of Technology, Oct. 1-2, 1997 pp. 21-26 (7 pages).

PCTUS07067424, Apr. 2007, Dental Implant Technologies, Inc., International Search Report.

Leu, et al., U.S. Appl. No. 60/748,787, Computer Aided Dental Bar Design, filed Sep. 9, 2005 (97 pages).

Bisler, et al., "The Virtual Articulator—Applying VR Technologies to Dentistry", Proceedings of the Sixth International Conference on Information Visualisation, IEEE Computer Society, 2002 (3 pages).

Üşümez, et al., "Inclinometer Method for Recording and Transferring Natural Head Position in Cephalometrics", American Journal of Orthodontics and Dentofacial Orthopedics, vol. 120, No. 6, Dec. 2001 pp. 664-670 (7 pages).

Kordaβ, et al., "The Virtual Articulator in Dentistry: Concept and Development", The Dental Clinics of North America, 46, 2002, pp. 493-506 (14 pages).

Murphy, et al., "The Development of Instrumentation for the Dynamic Measurement of Changing Head Posture", American Journal of Orthodontics and Dentofacial Orthopedics, vol. 99, No. 6, Jun. 1991, pp. 520-526 (7 pages).

Usumez, et al., "Effect of Complete Dentures on Dynamic Measurement of Changing Head Position: A Pilot Study", The Journal of Prosthetic Dentistry, vol. 90, No. 4, Oct. 2003, pp. 394-440 (7 pages).

Üşümez, et al., "Reproducibility of Natural Head Position Measured with an Inclinometer", American Journal of Orthodontics and Dentofacial Orthopedics, vol. 123, No. 4, Apr. 2003, pp. 451-454 (4 pages).

Delli, "Automated Design and Fabrication of Dental Bar", University of Missouri-Rolla, Nov. 17, 2006 (23 pages).

Leu, et al., "Computer-Automated Dental Bar Design", Technology/Business Opportunity, University of Missouri-Rolla, no date (2 pages).

Gawate, "Dental Bar Design (Thesis)", University of Missouri, Published 2005 (67 pages).

Taylor, "Influence of Computerized Tomography Parameters on the Quality of Stereolithographic Models (Thesis)". The University of Texas Graduate School of Biomedical Sciences, Mar. 1999 (102 pages).

\* cited by examiner

Centric Position

Protrusive Position

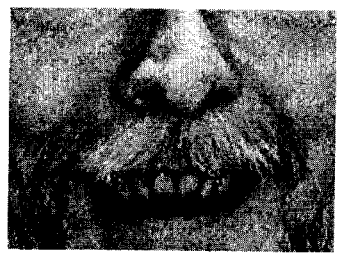 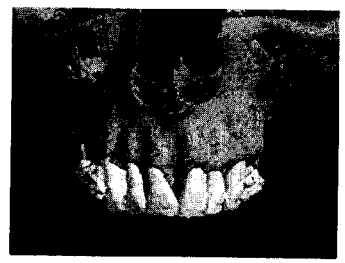 
Fig. 35A    Fig. 35B    Fig. 35C
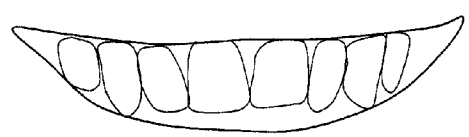
Fig. 35D

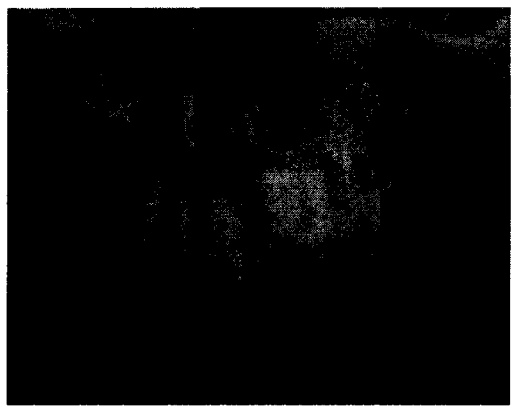 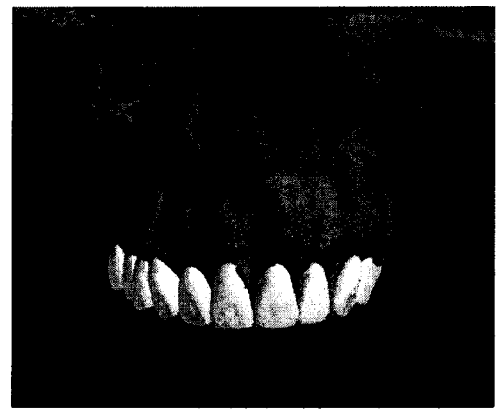
Fig. 36A Fig. 36B
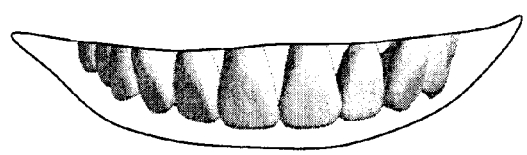
Fig. 36C

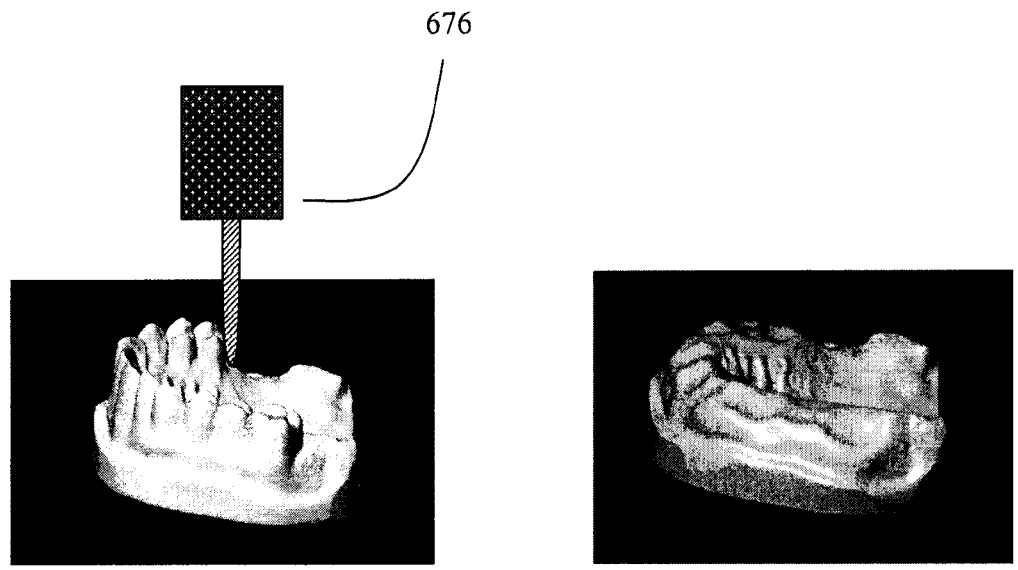
Fig. 38A
Fig. 38B
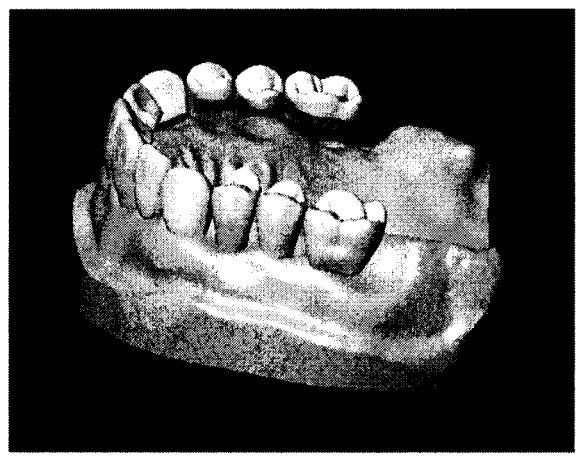
Fig. 38C

COMPUTER MACHINED DENTAL TOOTH SYSTEM AND METHOD

PRIORITY INFORMATION

This application claims priority to and the benefit of the filing date of the U.S. Provisional Application 60/794,996, filed Apr. 26, 2006, and is a continuation in part application of U.S. patent application Ser. No. 11/674,956, filed Feb. 14, 2007, which claims priority to and the benefit of the filing date of U.S. Provisional Application No. 60/773,433, filed Feb. 15, 2006, all of which are incorporated herein by reference in their entirety.

TECHNICAL FIELD

The present disclosure relates to a dental tooth system and method for constructing dental prosthetics, and in particular, dentures.

BACKGROUND

For over 70 years pre-fabricated denture teeth have been used to construct dentures. The teeth are manufactured from porcelain, plastic or composite materials. Many different shapes of teeth have been developed and patented to address specific treatment requirements. Construction of dentures with pre-fabricated teeth has many advantages over custom hand made teeth. The teeth are manufactured from specific molds and are of a consistent shape and quality. The porcelain or plastic materials can be made under controlled manufacturing conditions. The aesthetic appearance of the teeth is consistent and does not require carving the tooth form by hand. Unfortunately, there are problems with pre-fabricated teeth because the teeth are not custom made for each patient. As a result, hand grinding of the biting surfaces is often required to properly position the teeth for any given patient. It is also frequently necessary to grind the retentive surfaces of the teeth to allow them to fit to the shape of the residual alveolar ridge after natural teeth have been removed. Hand grinding is also required if the denture teeth are to fit to implant retained components. Denture teeth also frequently move during the process of packing and processing the denture base material to the denture teeth. This movement is called "processing error" and is corrected by hand grinding the teeth after processing.

Conventional Dentures

The selection of pre-fabricated denture teeth is usually based on the aesthetic requirements of the patient along with the form of the residual ridge and the muscular co-ordination of the patient. Some common types of teeth are: zero degree mono-plane teeth, anatomic teeth or teeth designed for "lingulalized occlusion." In the process of making dentures, a master impression is made of the upper and lower residual ridge and a dental cast is made by pouring a plaster type material into the impression to create a dental cast or model of the patient's mouth. This cast is then used to make record bases. Record bases are made of a light cured composite resin or autopolymerizing acrylic resin to provide a base to position and hold the artificial teeth in wax. In present art, each type of tooth is hand ground and set in a specific relationship to the residual alveolar ridge and the dental technician must carefully place each tooth in wax to maintain its ideal "set-up." This is a time consuming process well known in the art. If the teeth are to be set to a flat plane then a flat metal or plastic plate is used to position the biting surface of the tooth. If a balanced "lingualized occlusion" is used, teeth with prominent upper lingual cusps are set to a curved template with a radius of around 4 inches. Many different mechanical and anatomic reference points, planes and surfaces have been used to position artificial teeth by hand. The teeth are set in wax to maintain their position in relation to the record bases and to allow for a wax "try-in" which is an opportunity to try the tooth set-up in the patient's mouth to evaluate aesthetics and the position of the teeth. Wax is soft and can change shape when heated. Frequently denture teeth imbedded in wax will move even after being set in an ideal position. After the wax "try-in," the dentures are made by investing the teeth, wax and record base in a flask and heating it in a water bath to remove the wax and record base. The remaining space is filled with a heat or autopolymerizing denture base material. Processing the dentures causes the denture teeth to move during curing and after the base material has been processed to the teeth, a technician hand grinds the teeth to correct processing errors.

Immediate Dentures

Immediate dentures are made for patients that have many of their natural teeth, but the teeth are "hopeless" and will need to be surgically removed. Since most patients do not want to go without teeth during the period of healing, immediate dentures are made before the natural teeth have been extracted and are inserted at the time of surgery. The "set-up" of the artificial teeth can not be tried in the patient's mouth since the natural teeth are still present and the proper spatial position of the teeth in relation to the midline, anatomic landmarks and the opposing teeth is more difficult to determine. When making immediate dentures, the dental technician hand grinds the plaster cast of the patient's mouth to selectively remove the plaster teeth. This creates a cast that has a shape similar to the patient's mouth at the time of surgery after the teeth have been removed. The present laboratory process has some "guess work" since the dental technician does not know the shape of the bone supporting the teeth under the gum. These problems make immediate denture construction less predictable and more complex than conventional denture construction.

Conventional methods of constructing dentures may be labor intense, complex, and imprecise. There is a need for an improved denture tooth system and method that addresses these or other shortcomings in the prior art.

SUMMARY

Briefly stated, this disclosure is directed to a system, including apparatus and method to create a virtual computer model of a patient's mouth and to ideally position virtual denture teeth in proper spatial orientation to the supporting tissues, lips and opposing teeth. The positioning of denture teeth may be determined by the use of virtual planes, curved surfaces or other digital references. In some embodiments, the virtual set-up of denture teeth may be sent to the dentist treating the patient via the Internet to validate the proper tooth placement and aesthetics. This virtual set-up of pre-fabricated denture teeth may be then used to create an index to position and mill the real denture teeth and to position them in relation to the cast of the residual ridge. In some embodiments, the record base that holds the wax and denture teeth are fabricated with computer milling or computer layered manufacturing. In addition, errors in processing the denture teeth to the denture base material may be corrected by number controlled milling the biting surfaces of the denture teeth. This milling process also may be used to remove stone teeth and contour dental casts for patients that will be having immediate dentures.

In one exemplary aspect the present disclosure is directed to a method of manufacturing a dental prosthetic. The method may include arranging a first virtual tooth image relative to a second virtual tooth image on a virtual denture set and locating a first actual prosthetic tooth relative to a second actual prosthetic tooth in a manner corresponding to the arranged first and second virtual images. The method also may include performing at least one Boolean operation to remove a portion of the first virtual tooth image and the second virtual tooth image and machining the first actual prosthetic tooth and the second actual prosthetic tooth to remove a portion correspond to material removed by the Boolean operation performed on the first and second virtual tooth images.

In another exemplary aspect, the present disclosure is directed to a method of manufacturing a dental prosthetic. The method may include preparing a first try-in prosthetic having actual prosthetic teeth for a patient, the first try-in prosthetic being one of an upper dental prosthetic and a lower dental prosthetic and receiving information relating to alignment of the first try-in prosthetic within a patient's mouth relative to dental elements of the opposing arch. The method also may include recording the information relating to the alignment as virtual images and determining virtual interferences between the first try-in prosthetic and the dental elements of the opposing arch. It also may include machining the actual prosthetic teeth to remove interferences.

In another exemplary aspect, this disclosure is directed to a method of manufacturing a dental prosthetic. The method may include generating a virtual dental cast corresponding to an actual dental cast of a portion of a patient's inner mouth and generating a virtual record base and a virtual rim. It also may include virtually locating a virtual tooth image at desired location relative to at least one of the virtual dental cast, the virtual rim, and the virtual record base and locating an actual prosthetic tooth corresponding to the virtual tooth image on a corresponding location on the actual dental cast.

In another exemplary aspect, this discloser is directed to a method of manufacturing a dental prosthetic. The method may include generating a virtual image of a rim configured to fit an alveolar ridge of a patient and selecting a virtual tooth image of at least one tooth from a memory storing a plurality of virtual tooth images, the virtual tooth image corresponding to an actual prosthetic tooth. The virtual tooth image may be arranged at a desired location on the image of the rim and a Boolean operation may be performed to remove a portion of the virtual tooth image. A virtual positioning block overlapping the virtual tooth image may be created. The method also may include removing the virtual tooth image from the virtual positioning block to generate a virtual indentation in the virtual positioning block matching the virtual tooth and machining an actual positioning block to have an actual indentation corresponding to the virtual indentation. It also may include placing the actual prosthetic tooth into the indentation in the actual positioning block and generating first programming data for operating a tool cutting machine to cut a shape corresponding to the portion of the virtual tooth image removed by the Boolean operation, transferring the first programming data to the tool cutting machine, and machining the actual prosthetic tooth to remove material corresponding to the portion removed from the virtual tooth image by the Boolean operation. It also may include preparing a first try-in prosthetic including the actual prosthetic tooth for the patient, the first try-in prosthetic being one of an upper dental prosthetic and a lower dental prosthetic. The method further may include receiving information relating to alignment of the first try-in prosthetic within the patient's mouth, recording the information relating to the alignment as virtual images, and determining virtual interferences between the first try-in prosthetic and patient's opposing dental elements. At least a part of the virtual interferences in the virtual image may be removed by a Boolean operation. Second programming data may be generated for operating a tool cutting machine to cut shapes corresponding to the virtual interferences removed by the Boolean operation. The second programming data may be transferred to the tool cutting machine, and the actual prosthetic tooth may be machined to match the virtual tooth image and remove the real interferences.

In yet another exemplary aspect, the present disclosure is directed to a method of manufacturing an immediate denture. The method may include generating a virtual image of a dental cast, the virtual image including the teeth of the dental cast. It also may include virtually removing the teeth from the virtual image to create a virtual alveolar ridge and selecting a virtual tooth image from a memory storing a plurality of tooth images, the virtual tooth image corresponding to an actual prosthetic tooth. The method also may include arranging the virtual tooth image at a desired location on the virtual image of the virtual alveolar ridge and may include using a Boolean operation to remove a portion of the virtual tooth image. Programming data may be generated for operating a tool cutting machine to cut shapes corresponding to the portion of the virtual tooth image removed by the Boolean operation. The programming data may be transferred to the tool cutting machine, and the actual prosthetic tooth may be machined to remove material to match the virtual tooth image.

In yet another exemplary aspect, the present disclosure is directed to a method of treating a dental patient. The method may include scanning the patient's head with a CT scanner to generate a virtual head image of the patient's head, removing the patient's virtual teeth from the virtual head image, and selecting a virtual tooth image from a memory storing a plurality of tooth images, the virtual tooth image corresponding to an actual prosthetic tooth. The method also may include arranging the virtual tooth image at a desired location on the virtual head image and displaying the virtual tooth image in the virtual head image.

In one exemplary aspect, this disclosure is directed toward a system for manufacturing a dental prosthetic. The system may include means for arranging a first virtual tooth image relative to a second virtual tooth image on a virtual denture set and may also include means for locating a first actual prosthetic tooth relative to a second actual prosthetic tooth in a manner corresponding to the arranged first and second virtual images. The method further may include means for performing at least one Boolean operation to remove a portion of the first virtual tooth image and the second virtual tooth image, and means for machining the first actual prosthetic tooth and the second actual prosthetic tooth to remove a portion correspond to material removed by the Boolean operation performed on the first and second virtual tooth images.

In yet another exemplary aspect, this disclosure is directed to a system of manufacturing a dental prosthetic. The system may include means for preparing a first try-in prosthetic having actual prosthetic teeth for a patient, the first try-in prosthetic being one of an upper dental prosthetic and a lower dental prosthetic, and may include means for receiving information relating to alignment of the first try-in prosthetic within a patient's mouth relative to dental elements of the opposing arch. The system further may include means for recording the information relating to the alignment as virtual images, means for determining virtual interferences between the first try-in prosthetic and the dental elements of the opposing arch, and means for machining the actual prosthetic teeth to remove interferences.

In another exemplary aspect, the present disclosure is directed to a system of manufacturing a dental prosthetic. The system may include means for generating a virtual dental cast corresponding to an actual dental cast of a portion of a patient's inner mouth, means for generating a virtual record base and a virtual rim, means for virtually locating a virtual tooth image at desired location relative to at least one of the virtual dental cast, the virtual rim, and the virtual record base, and means for locating an actual prosthetic tooth corresponding to the virtual tooth image on a corresponding location on the actual dental cast.

In yet another exemplary aspect, the present disclosure is directed to a system of manufacturing an immediate denture. The system may include generating a virtual image of a dental cast, the virtual image including the teeth of the dental cast. The system also may include means for virtually removing the teeth from the virtual image to create a virtual alveolar ridge and means for selecting a virtual tooth image from a memory storing a plurality of tooth images, the virtual tooth image corresponding to an actual prosthetic tooth; Additionally, the system may include means for arranging the virtual tooth image at a desired location on the virtual image of the virtual alveolar ridge, means for using a Boolean operation to remove a portion of the virtual tooth image, and means for generating programming data for operating a tool cutting machine to cut shapes corresponding to the portion of the virtual tooth image removed by the Boolean operation. The system may further include means for transferring the programming data to the tool cutting machine; and means for machining the actual prosthetic tooth to remove material to match the virtual tooth image.

In yet another exemplary aspect, the present disclosure is directed to a system of treating a dental patient. The system may include means for scanning the patient's head with a CT scanner to generate a virtual head image of the patient's head and may include means for removing the patients virtual teeth from the virtual head image. Further, the system may include means for selecting a virtual tooth image from a memory storing a plurality of tooth images, the virtual tooth image corresponding to an actual prosthetic tooth, means for arranging the virtual tooth image at a desired location on the virtual head image, and means for displaying the virtual tooth image in the virtual head image.

BRIEF DESCRIPTION OF THE DRAWINGS

FIG. 22 B is an illustration of an exemplary tooth in relation to the residual alveolar ridge and an exemplary implant component.

FIG. 24 B illustrates an exemplary actual plaster reference block on a 3 axis mill.

FIG. 35 is a picture of the patient's smile (A), an exemplary 3D rendering of CT data to create a model of teeth and upper jaw (B), an exemplary 3D rendering of CT data for upper jaw and scan data of the upper cast to create composite view of CT and cast data (C), and line drawing of shape of lips and teeth to be removed (D).

FIG. 36 is an illustration of the virtual model of the upper jaw with teeth removed (A) using Boolean computer operations, an illustration of virtual model of upper jaw with virtual denture teeth positioned for the construction of immediate dentures (B), and a view of patient's lips and virtual set-up of denture teeth (C).

FIG. 38 is an illustration of a dental cast with teeth to be used to make an immediate denture on a mill (A), an illustration of the same cast after being cut with the mill to create the shape of the mouth after the teeth have been removed (B), and with the virtual position of the denture teeth illustrated (C).

DETAILED DESCRIPTION

Figure 1:
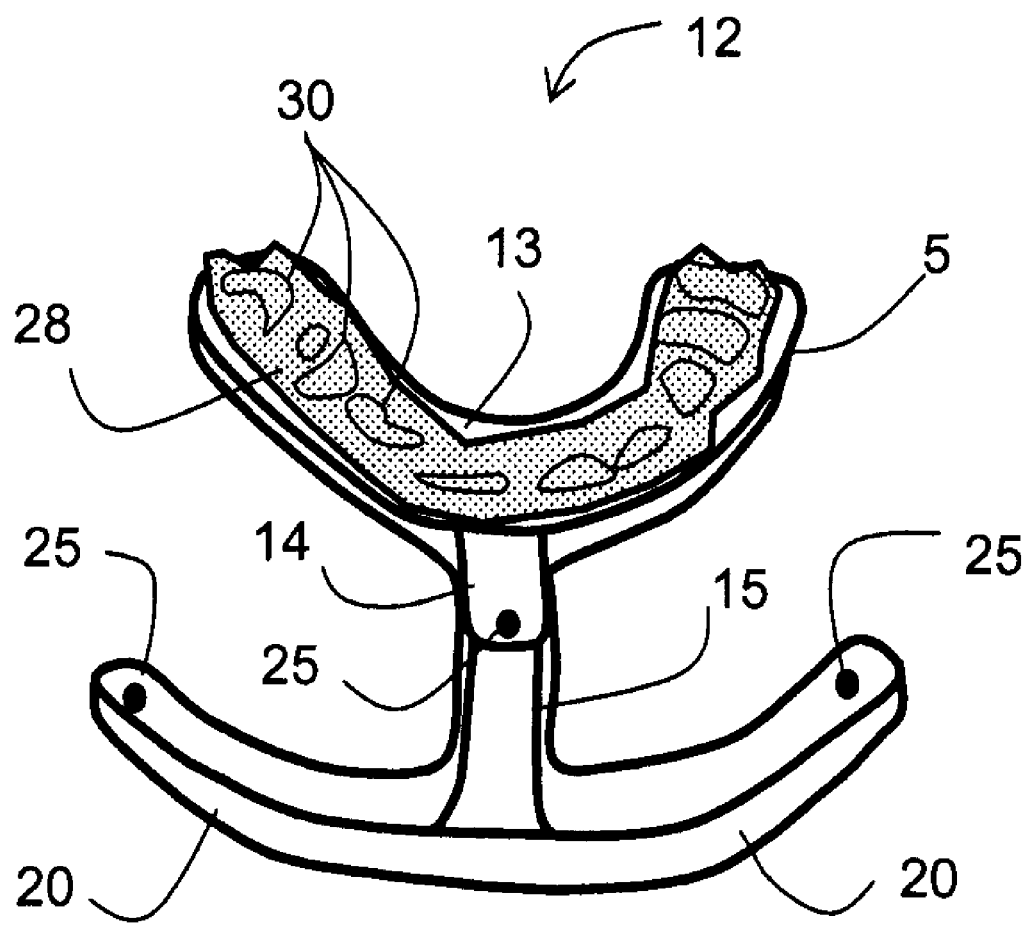
FIG. 1 is a schematic view of an exemplary CT bite plate with bite registration material.

For the purposes of promoting an understanding of the principles of the invention, reference will now be made to the embodiments, or examples, illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

Making a Computer Model of the Jaws

A radiolucent CT bite plate may be used to record the position of the patient's teeth during CT imaging. The CT bite plate may be rigid and may include three or more non-linear radiographic markers imbedded in it. Bite registration material may be placed on the bite plate and the patient may bite into the material to record a specific jaw position. The bite plate may include an extension that projects through the lips and extends vertically away from the plane of occlusion and laterally around and away from the soft tissues of the face. The radiographic markers can be detected in the CT image but do not create scatter. The bite plate may then be used at the time of CT imaging to position the patient's teeth and jaws in a known relationship and to create radiographic images of the position of the bite plate in the CT scan. If a cone beam machine is used that allows the patient to sit upright, the head is positioned in natural head position or any other diagnostic position that is required for aesthetic and diagnostic analysis. The resulting image will have the position of the teeth and soft tissues recorded in relation to horizontal.

A digital data set may also be made of the patient's teeth and soft tissues using non-radiographic imaging of the teeth and tissues directly in the mouth with photographic, light, laser, holographic or any other imaging system that will record the teeth with an acceptable precision. An alternative process is to make conventional dental impressions of the upper and lower jaws and to then image the dental casts made from the impressions. If dental casts are made, the casts can be scanned with contact digitizing in addition to the above mentioned processes. For data sets made from dental casts, the jaw position may be recorded using the CT bite plate. If the teeth are scanned directly in the mouth, the relationship of the upper and lower jaw may be recorded by imaging the surfaces of the teeth in both arches at the same time with the patient biting into the CT bit plate. Alternatively, the arches may be separately scanned.

If dental casts of the upper and lower jaws are made, a preferred embodiment is to use a cast holder to record the position of the upper and lower dental cast in relation to the CT bite plate. The casts may be joined to mounting plates that record their relationship to the CT bite plate and the cast holder. The mounting plates may include magnetic or mechanical fixation systems that join the mounting plates to receivers on the cast holder. Casts can then be removed from the cast holder in a known spatial relationship to the receiver. The casts can then be moved to the imaging system for imaging. Since the data sets for the upper and lower dental cast are known in relation to the mounting plates and cast holder, data sets from the upper and lower casts can be moved in computer space such that the same three-dimensional orientation exists in computer space as existed when the bite plate was in the mouth. This creates an accurate virtual computer model of the upper teeth and tissues in relation to the lower teeth and tissues in a specific static orientation. The computer models and fixation device should record the form of the teeth and the positional relation of each data set to a high level of precision since patients can feel an object 12 microns thick between their teeth.

The computer model of the upper and lower jaws just described can be very precise but it does not have information about the shape of the bone supporting the teeth or the position of nerve canals and other information obtained using CT. The present invention solves this problem by imaging the patient's head and jaws with CT using the CT bite plate. The CT data set may be made with the patient biting into the CT bite plate and may orient the data set to three radiographic markers that allow the information to be moved in computer space such that three dimensional data sets for the dental casts or teeth made using non-radiographic techniques are in the same orientation as the CT data set. Finally, the patient's head can be positioned during the CT scan such that a normal position (natural head position) or any other diagnostic position can be recorded. This will allow for the precise analysis of the orientation of the teeth to the eyes, face, lips, ears, horizontal or any other diagnostic reference point recorded during the scan.

The computer model made using the described invention creates a precise static model of the patient in a specific jaw position. Movement of the computer model can be created by using data from the CT scan to determine the orientation of the upper teeth to the condyles and rotational centers. This is commonly done in the dental art by using a face bow to approximate the position of the condyles using the ear hole opening as a guide. The actual condyles imaged in the CT can also be used and information about the shape of the condylar fossae may also be a good approximation of movement. This invention also provides for the incorporation of data sets from commercial digital recording devices. These devices record movement of the lower jaw in relation to the upper jaw and since a static starting point has been recorded with the CT bite plate, it is a simple process to produce motion of the lower jaw model from that point in virtual computer space.

Turning now to the figures, FIG. 1 illustrates an exemplary CT bite plate assembly 12 that may be used when capturing a CT of a patient's teeth. The bite plate assembly 12 may include a U-shaped rigid section 5 attached to a thin bite surface 13 made of a radiolucent material that mates with the patient's teeth and yet requires minimal opening of the jaws. The bite surface 13 may include a central forward projection 14 that extends between the lips when the assembly 12 is placed in a patient's mouth. The forward projection 14 may be joined to a vertical portion 15 that, in some embodiments, extends above or below the plane of occlusion. Wings 20 extend laterally from the vertical portion and follow the contour of the face but do not contact it. In this exemplary embodiment, three or more non-linear radiographic markers 25 are attached to the vertical and wing portions of the CT bite plate. These markers 25 have a radiographic density that makes them visible in the CT data and also have a geometric shape that can be imaged with contact, light, laser, or holographic imaging techniques. Bite registration material 28 may be used to record the indentations 30 of the upper and lower teeth when the patient bites into the CT bite plate assembly 12.

In some examples, except for the radiographic markers, the CT bite plate assembly is formed entirely of a substantially radiolucent material. Accordingly, as described below, images captured by a CT machine may clearly display the radiographic markers 25 while less clearly showing the CT bite plate assembly 12. In some embodiments, the radiographic markers 25 are disposed above or below the plane of occlusion formed by the upper and lower teeth. This may enable better imaging and may reduce the chance of the image of the radiographic markers 25 being skewed by its position relative to other radiographic materials in the mouth, such as dental treatment devices, including fillings, crowns, and braces, among others. The exemplary CT bite plate assembly 12 in FIG. 2 includes three radiographic markers. In yet other exemplary embodiments, the CT bite plate assembly may include two or more than four radiographic markers 25 that are disposed above or below the plane of occlusion.

Figure 2:
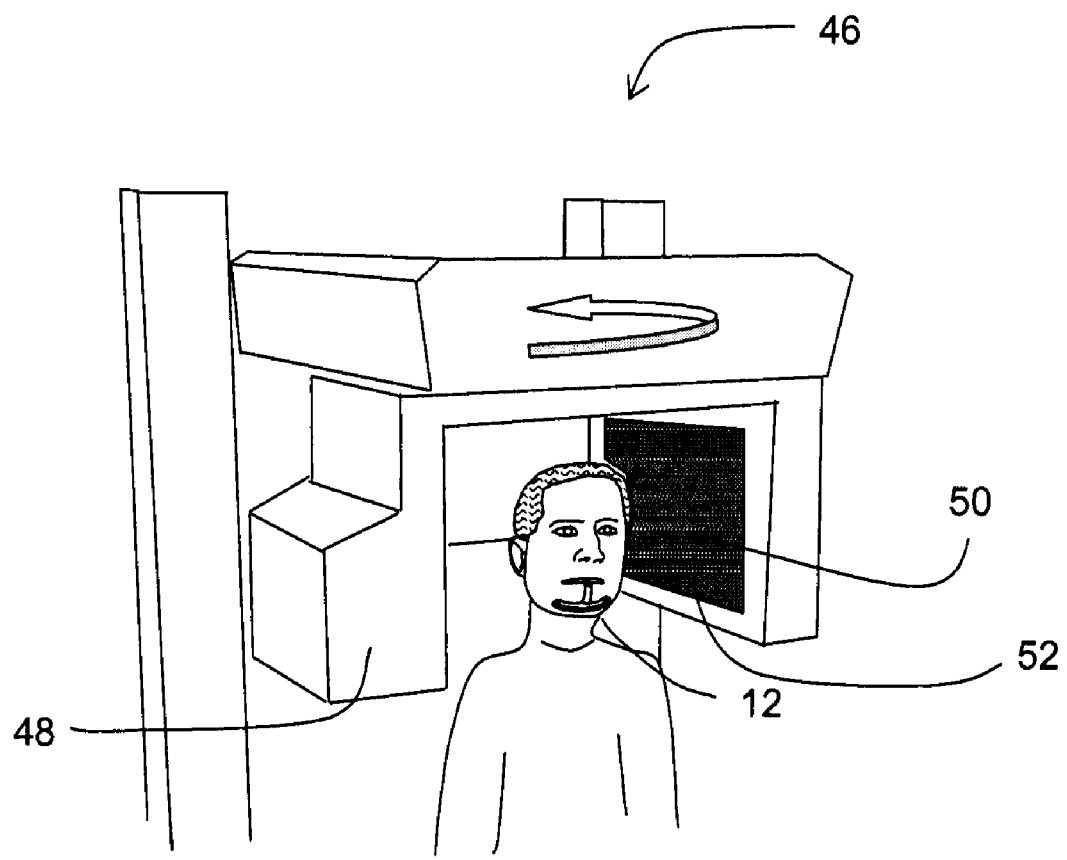
FIG. 2 is a schematic view illustrating the positioning of a patient in a cone beam CT machine with the CT bite plate in the mouth.

FIG. 2 illustrates the CT bite plate assembly 12 placed in a patient's mouth and the patient positioned in a CT machine 46. The x ray source 48 projects radiation across the patient's head and is detected on a rectangular shaped sensor or detector 50. In this example, the patient's head is positioned in a natural posture in relation to the floor and to the horizontal edge of the detector 52. As the x ray source 48 and detector 50 rotate around the patient, the normal head posture may be recorded in the scan data. In some exemplary embodiments, the CT machine is a cone beam CT unit.

Conventional scanning operations may include orienting the patient's head in a position that is not the natural position. The term "natural position," as used herein, refers to a forward facing person appearing as they would in a social setting. Because the image itself includes no reference points, in order to capture the teeth in a known, reproducable orientation, the patient may be required to hold his head or bend his neck in an unnatural position during capturing. Then, the physician can make a treatment plan based on the known orientation. These positions, while still allowing capturing of desired spatial relationships between facial features, may not create a realistic image of the patient's natural posture because the head was not in a natural position during scanning, and there is no reference that later tells the physician when the head image is oriented in the natural position. Accordingly, using the captured images to create treatment plans that involve jaw and teeth displacement may consider the patient's appearance in an un-natural posture, providing an appearance that often differs from the patient's natural appearance.

In contrast, scanning the patient's head in a natural position or posture in relation to the floor or in relation to the horizontal edge of the detector may be advantageous when the captured images are used to create a treatment plan affecting aesthetics. Because the scan is taken with the head in a natural position, the aesthetic position of the teeth, head, eyes, lips, ears, and any other soft or hard tissue can be measured and recorded as the patient would appear to others in social settings, instead of with his or her head tilted back or otherwise placed in an unnatural position. Thus, the natural position of the head is known relative to the horizontal edge of the detector. While developing a treatment plan, the physician can return the image of the head to the natural position for analysis. Further, because the natural position of the head image is known relative to the horizontal edge of the detector, the image still may be manipulated to positions other than the natural position if desired.

Thus, unlike prior systems that capture images in an unnatural position relative to a fixed reference point, the system disclosed herein may capture images in a natural position relative to a fixed reference point, such as a horizontal edge of the detector. A physician then, while manipulating a CT image, can always return the image to the reference point to return to the natural position.

Figure 3:
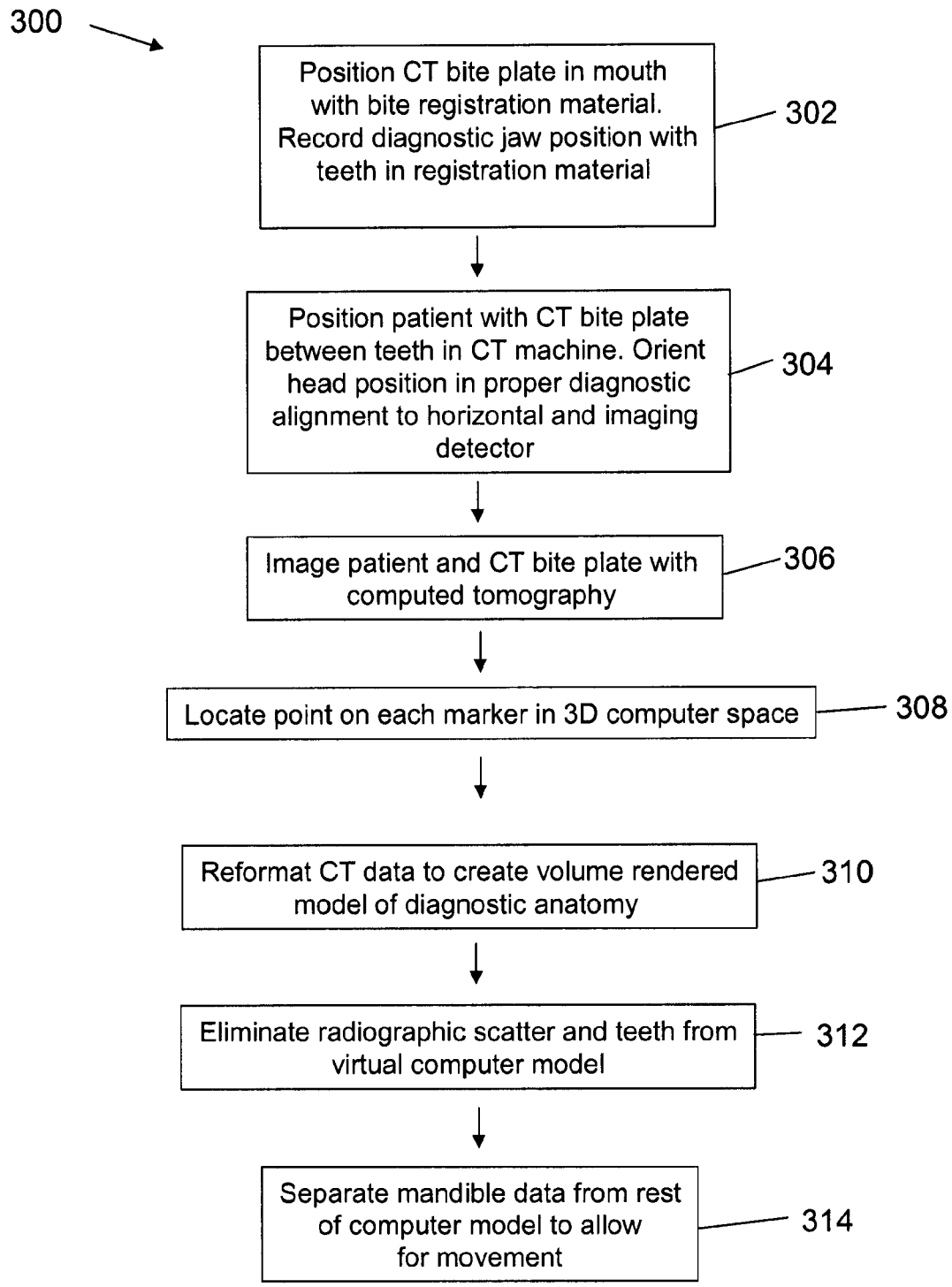
FIG. 3 is a flow chart showing an exemplary process for CT imaging the patient with the CT bite plate, the process of selecting points on radiographic markers, and process of eliminating teeth and radiographic scatter

Recording the CT image is described in more detail with reference to a flow chart, identified by the reference numeral 300, in FIG. 3. In short, FIG. 3 shows an exemplary process of imaging the patient with CT, locating three points in the CT data, and eliminating teeth and radiographic scatter. The process begins with placing or positioning the CT bite plate assembly 12 in the patient's mouth, at a step 302. Here, the bite plate assembly 12 may include the registration material for taking an impression of the patient's upper and lower teeth.

At a step 304, the patient is positioned, with the CT bite plate between his teeth, in a CT machine. The patient's head is positioned in proper diagnostic alignment to horizontal and to the imaging detector. Accordingly, the patient's head is held in a natural position, rather than an unnatural position. To position the patient's head, he or she may be instructed to look at a location, such as a mirror or point on a wall, that is disposed relatively horizontally from his or her head.

At a step 306, the patient and the CT bite plate 12 are imaged with computed tomography. If the CT bite plate 12 includes the registration material, then the diagnostic jaw position is recorded with the patient's teeth in the registration material.

At a step 308, a point on each marker is located in 3D computer space. In some exemplary embodiments, the point on the marker may be the most superior point on the surface of the marker. Other points on the marker may be used with equal success, such as for example, the lowermost point, a side location or a tip of a pointed marker.

Figures 8A, 8B:
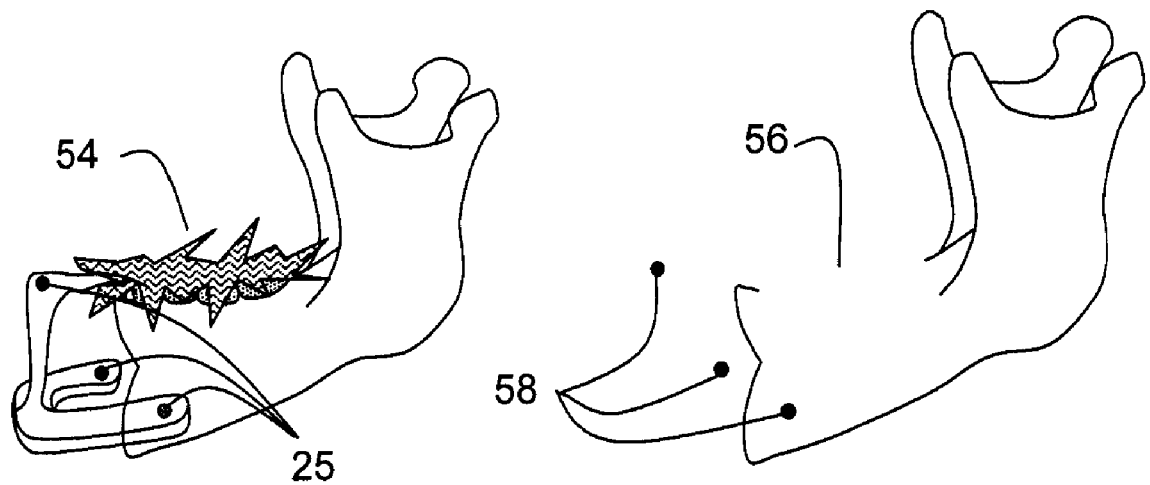
FIGS. 8A and 8B are illustrations of exemplary rendered data from CT imaging with the radiograph scatter present (as in FIG. 8A) and removed (as in FIG. 8B).

At a step 310, the collected CT data is reformatted to create a volume rendered model of the diagnostic anatomy of the patient. While the collected CT data may be used to create a full model of the diagnostic anatomy of the head and face of the patient, FIG. 8A shows one example of only a part of the full model of the diagnostic anatomy. In FIG. 8a, mandible data of the full model is shown with the three radiopaque markers 25 and with the radiographic scatter 54 due to dental fillings and crowns. This scatter makes the CT data set for the teeth non diagnostic. Returning to FIG. 3, at a step 312, the radiographic scatter is eliminated, along with the teeth from the virtual computer model. FIG. 8B illustrates the altered file with the teeth and radiographic scatter removed 56 and the radiographic markers replaced as precise points 58 located from the CT bitmap of the markers.

At a step 314, the mandible data is separated from the rest of the computer model, as is shown in FIGS. 8A and 8B, to allow for movement of the mandible independent of the rest of the computer model. This provides the ability to analyze jaw movement and develop a treatment plan consistent with desired jaw movement.

Figure 4A:
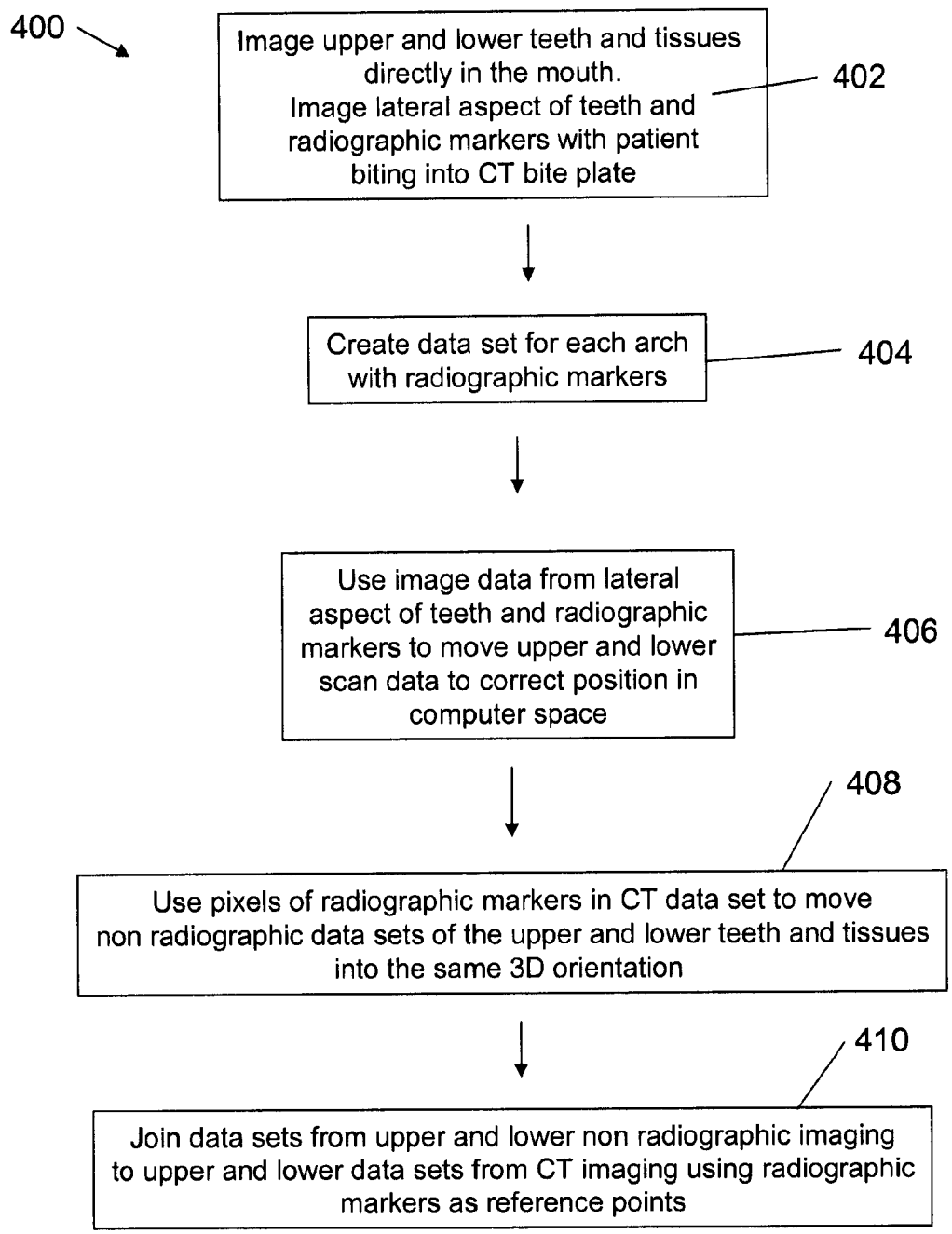
FIGS. 4A and 4B are flow charts showing exemplary processes of non-radiographic imaging of a patient's teeth and radiographic markers. Joining CT data sets with obtained non-radiographic data sets is also illustrated.
Figure 4B:
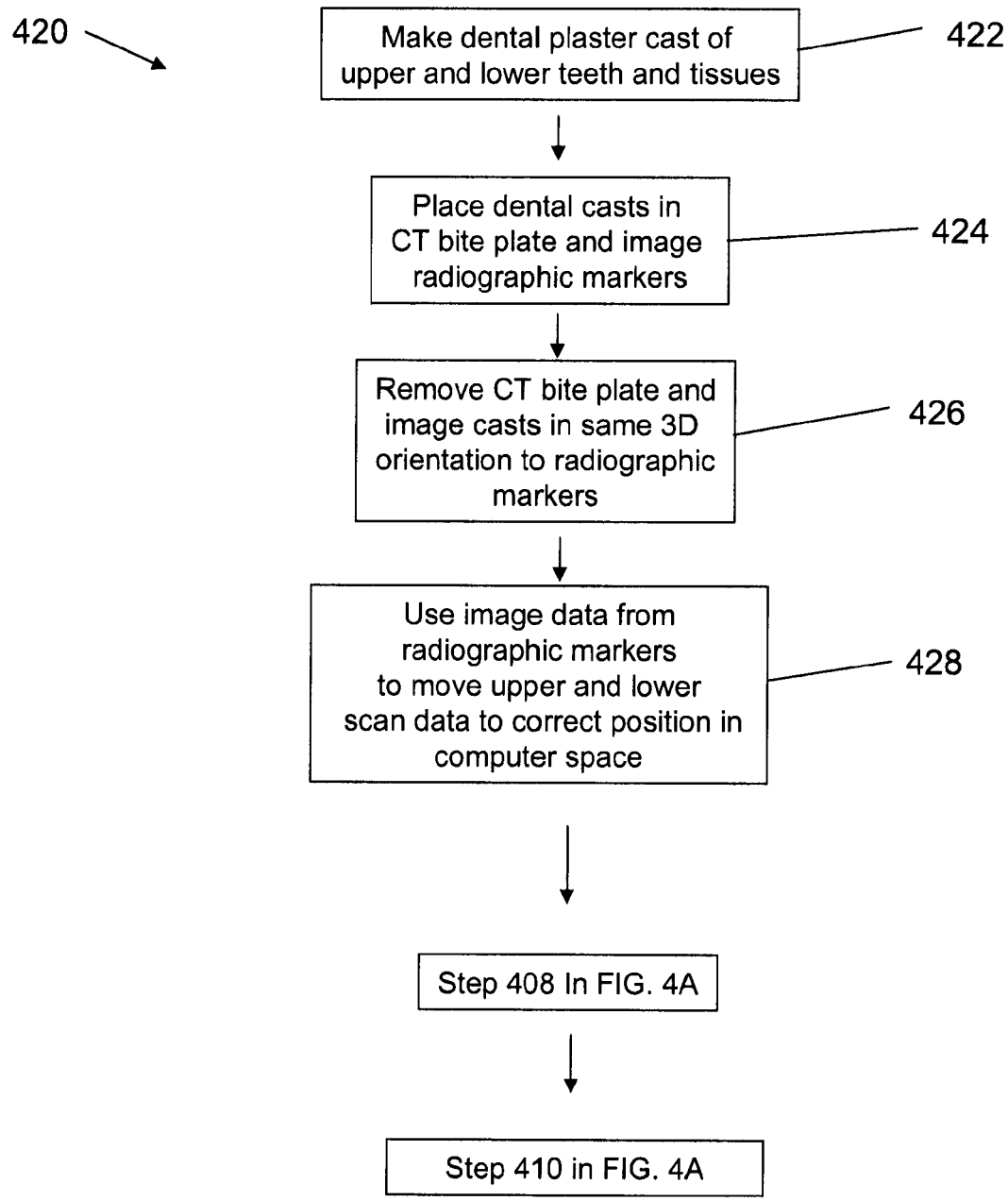

Either before or after the CT image is obtained as described in the flow chart 300, a non-radiographic image of the patient's teeth also may be obtained. FIG. 4A illustrates an exemplary process of non-radiographic imaging the patient's teeth directly in the mouth and FIG. 4B illustrates the process of imaging dental casts to create a data set of the teeth tissues and radiographic markers.

Referring first to FIG. 4A, a process for generating a non-radiographic image is shown in a flow chart, referred to by the reference numeral 400. The process begins at a step 402 by inserting the CT bite plate 12 into the patient's mouth and imaging the upper and lower teeth and tissue directly in the mouth. Also at this time an image is taken of a lateral aspect of the teeth and the radiographic markers with the patient biting into the CT bite plate. These images may be taken using non-radiographic imaging devices, such as laser devices, light devices, or holographic devices to image the teeth.

At a step 404, a data set is created for the top arch and a data set is created for the bottom arch. Each of these data sets also includes data representing the radiographic markers.

At a step 406, the image data of the lateral aspect of the teeth and of radiographic markers may then be used as a reference to move and locate the upper and lower scan data to a correct position in the computer space.

Figure 9:
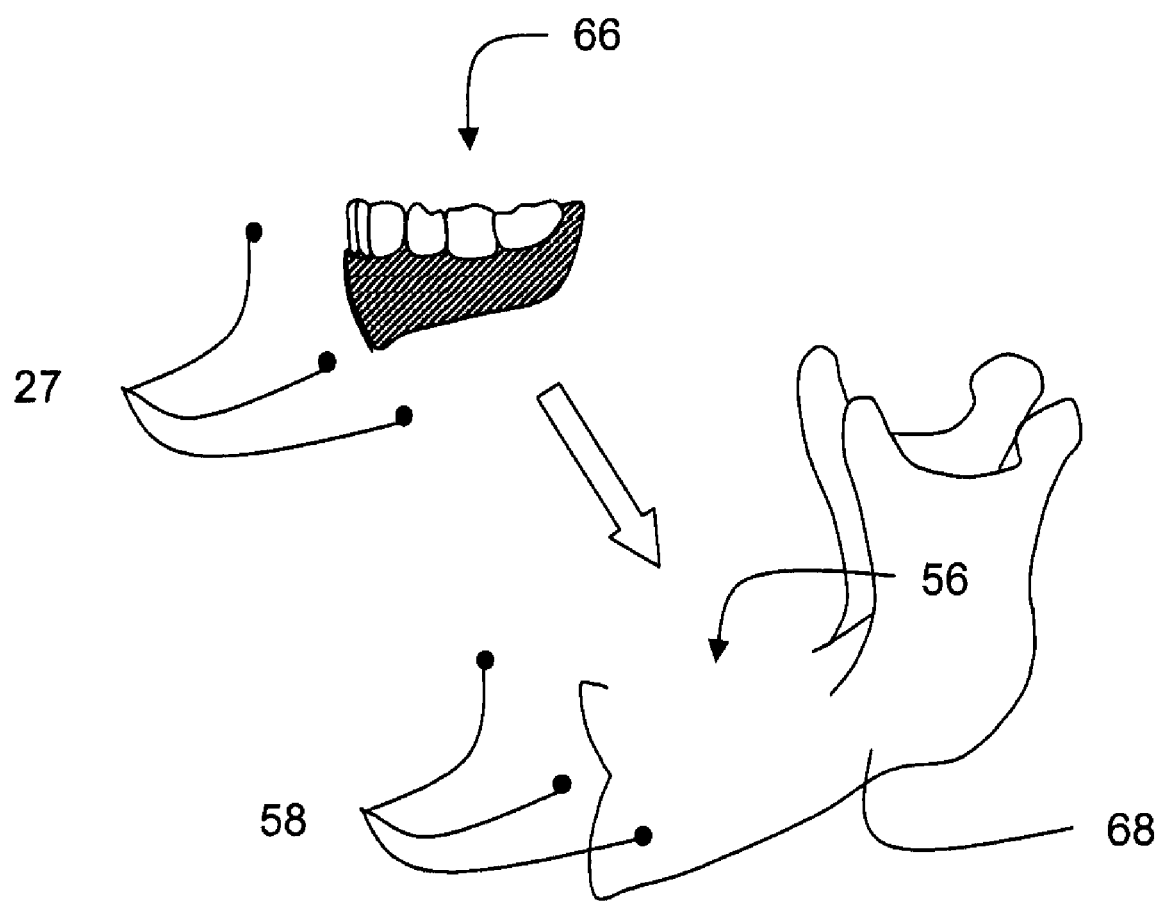
FIG. 9 illustrates exemplary non-radiographic data set of the lower teeth being joined to an exemplary CT data set of the mandible using the radiographic markers for orientation.

The CT data set and the non-radiographic data set are then brought together. At a step 408, pixels of the radiographic markers in the CT data set are used as references to move the non-radiographic data sets of the upper and lower teeth and tissues into the same 3D orientation. FIG. 9 shows one example of how this may appear, but shows only the lower teeth and jaw, with the non-radiographic imaging of the teeth 66 and the CT scan data 68.

Finally, at a step 410, the data sets from the upper and lower non-radiographic imaging are joined to the upper and lower data sets from CT imaging using the radiographic markers as reference points. Joining may be accomplished using Boolean operations and may occur for both the upper teeth set and for the lower teeth set.

Another exemplary process of capturing a non-radiographic image is described with reference to a flow chart, referenced as 420 in FIG. 4B. Here, at a step 422, a dental plaster cast is made of the upper and lower teeth and tissues. These may be made in any conventional manner.

Figure 6:
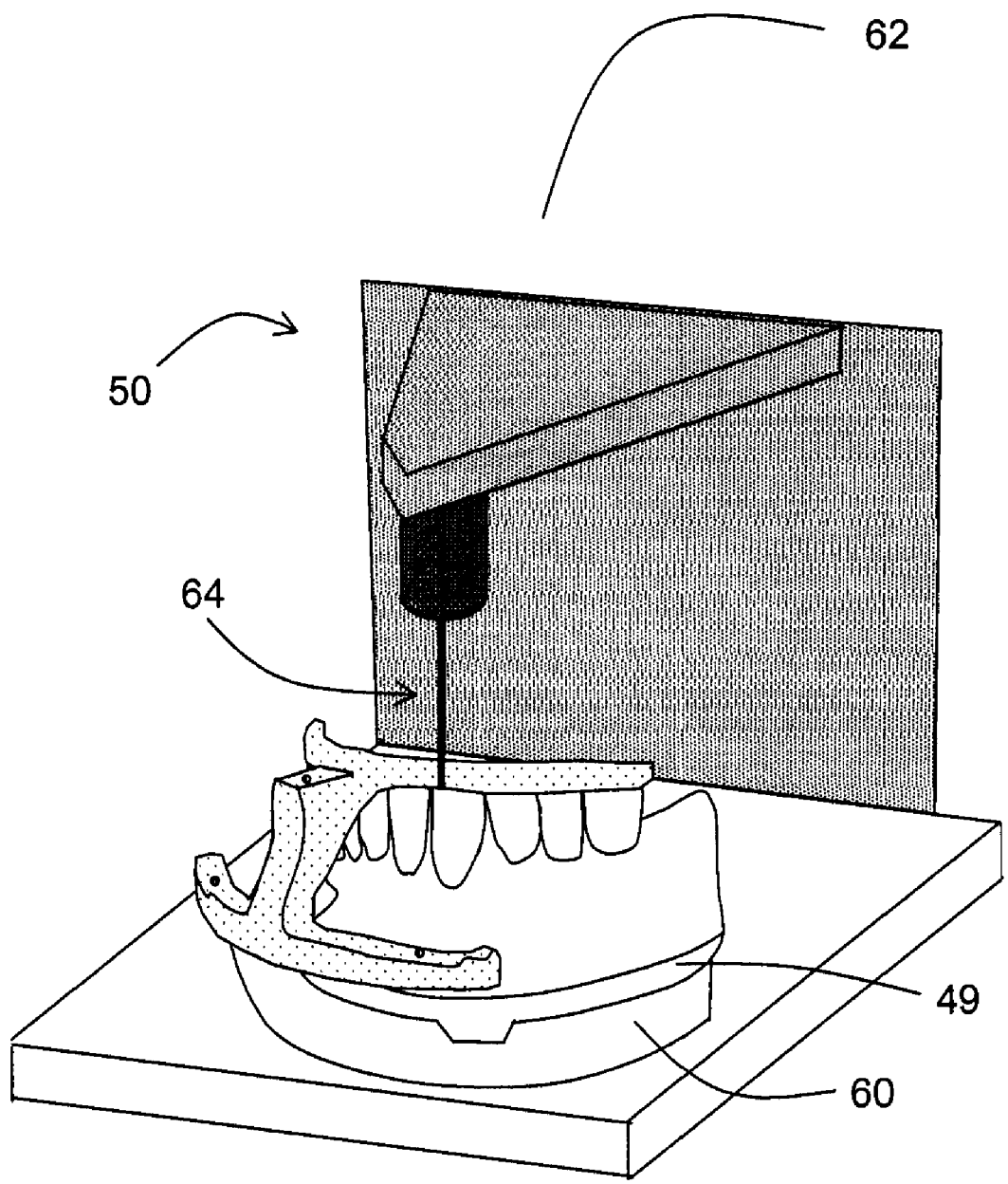
FIG. 6 is a schematic of an exemplary non-radiographic imaging system.
Figure 7:
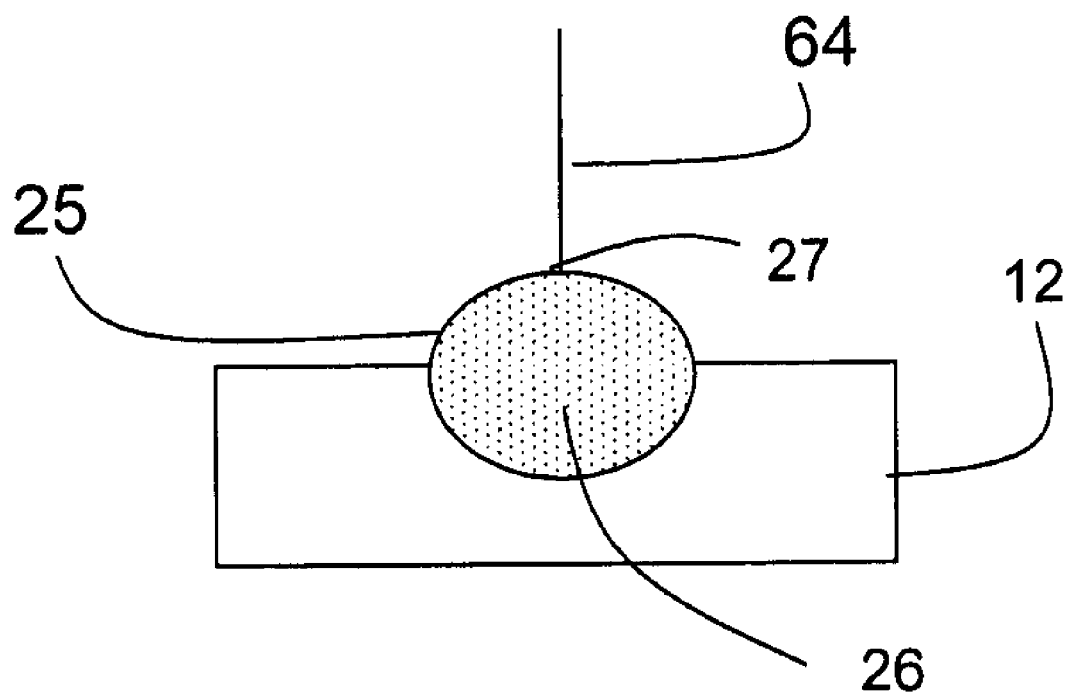
FIG. 7 is a schematic of an exemplary radiographic marker.

At a step 424, the dental casts are placed in the CT bite plate 12 and the radiographic markers are imaged by a scanning machine. One example of this is shown in FIG. 6, where the lower cast is shown with the CT bite plate. Here, the radiographic markers are being imaged by a contact digitizer. A closer view is shown in FIG. 7, where a specific point on the marker 25 may be digitized for later reference.

At a step 426, the CT bite plate is removed and the upper and lower casts are imaged in the same 3D orientation as was the radiographic markers. Accordingly, the dental casts are imaged relative to the radiographic markers in the CT bite plate 12. Once one of the upper and lower casts is imaged, the other also may be imaged. Separate imaging of the upper and lower casts enables easier analysis for treatment, as described further below.

At a step 428, image data from the radiographic markers may be used to orient the scan data of the upper and lower casts and move them to correct positions in the computer space. Then, at step 408, as described above with reference to FIG. 4A, pixels of radiographic markers in the CT data set are used as reference points to move and orient the non-radiographic data sets of the upper and lower teeth and tissues into the same 3D orientation. At step 410, the data sets from the upper and lower non-radiographic imaging are joined to the upper and lower data sets from CT imaging using the radiographic markers as reference points.

Figure 5:
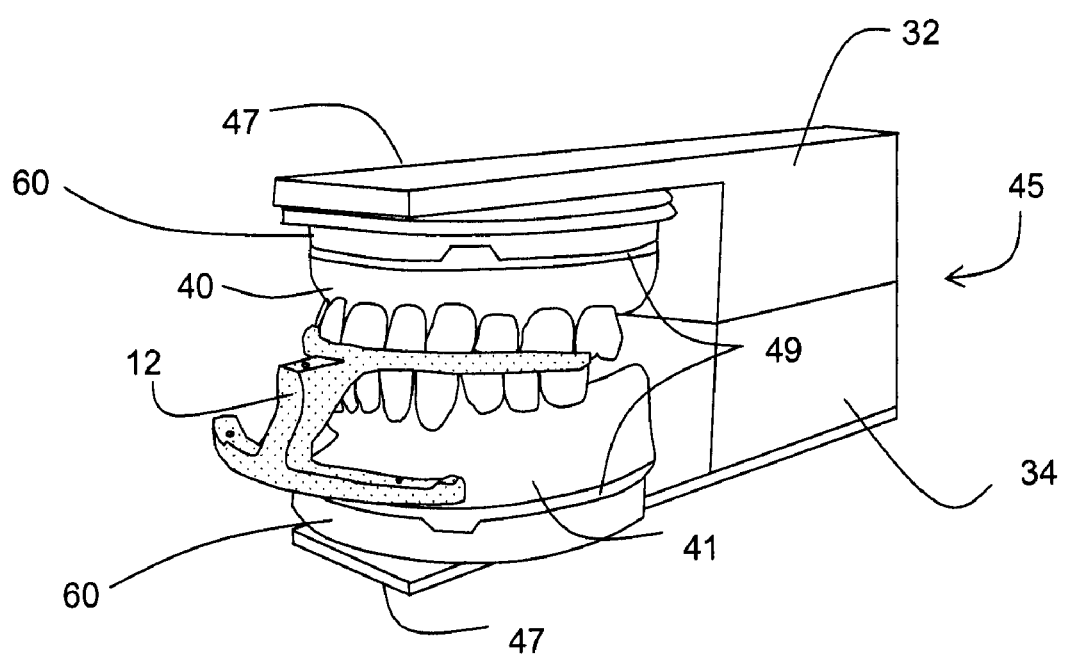
FIG. 5 illustrates an exemplary cast holding device and exemplary reference plates.

FIG. 5 illustrates an exemplary upper dental cast 40 and an exemplary lower dental cast 41 positioned into the CT bite plate 12 to reproduce the precise jaw position made in the CT scan. The cast holder 45 is a mechanical device that has an upper member 32 and lower member 34 that can be separated and repositioned into the exact same orientation. Each cast is also joined to a mounting plate 49 that precisely connects to the upper and lower member of the cast holder with a mechanical or magnetic receiver 60. After mounting the casts in the cast holder, the upper and lower dental casts can be removed and placed in the imaging system. The digital imaging system can use any number of methods that include laser, light, holographic or contact digitizing to image the dental casts and the CT bite plate.

FIG. 6 illustrates one exemplary embodiment using contact digitizing to create a data set of the lower cast with and without the CT bite plate and the upper cast. The CT bite plate and the lower cast are moved to the scanner 62 from the cast holder and the cast and CT bite plate are positioned in the receiver 60 and scanned. The probe of the scanner 64 creates a data set of the surface of the CT bite plate on the lower cast. The contours of the radiographic markers are scanned with the probe and the precise location of the markers recorded in three-dimensional computer space. A second scan is made of the lower cast with the CT bite plate removed from the cast, thereby providing an accurate digital data set for an image of the lower cast. Finally, the upper cast is placed in the receiver 60 and scanned. Since the orientation of the upper cast relative to the lower cast is known and reproduced with the cast holder 45 it is possible to move the data set for the upper cast in three-dimensional computer space to the exact relationship that existed when the casts were mounted in the cast holder In some examples, the upper and lower casts are placed within the scanner in a fully occluded position, not separated by the CT bite plate. In this position, the upper and lower casts are scanned together. The CT bite plate may then be inserted between the upper and lower casts, and then may be imaged to measure the separation generated by the CT bite plate. Thus, the second scan will correspond in separation distance to the full CT image, including the CT bite plate.

FIG. 7 illustrates a radiographic marker with a specific geometric shape that can be scanned easily with the contact digitizer. One example is a sphere 26 that is attached to the CT bite plate 12. The probe from the contact digitizer records a data set for the exposed surface of the spherical radiographic marker and a specific point with an x, y, and z location can be recorded 27. A useful example is the most superior point on the surface of the sphere. The same point can be located on the data set from the CT scan of the patient. This data will be represented as grayscale bitmaps. The pixel that represents the most superior pixel on the radiographic image can also be easily located and recorded. By locating three non-linear points on markers in the CT data as well as the contact digitizing data it is possible to move the data sets for the upper and lower cast into the same orientation as existed for the CT scan data. This creates a virtual model of the CT data as well as the contact digitizing data in the same three-dimensional computer space.

The CT data set is then reformatted as a 3D computer model such as a stereolithography (.stl) image or any number of 3D computer renderings. FIG. 8A illustrates the reformatted scan data from CT imaging with the three radiopaque markers 25 and radiographic scatter 54 due to dental fillings and crowns. This scatter makes the CT data set for the teeth non diagnostic. FIG. 8B illustrates a portion of the altered .stl file with the teeth and radiographic scatter removed 56, as described in FIG. 3, and the radiographic markers replaced as precise points 58 located from the CT bitmap of the markers.

FIG. 9 illustrates the scan data from non-radiographic imaging of the teeth 66. Three points 27 indicate the position of the markers in the scan data. The CT scan data 68 with points representing the radiographic markers 58 are illustrated with the radiographic scatter removed 56. It is then possible to move the computer data representing the teeth 66 to its correct spatial position in relation to the CT data 68 using a three point move from the points recording the marker positions 27 to the computer position represented in the CT scan indicated by points 58. Once moved, the radiographic and non-radiographic data can be joined using Boolean operations. The same process can be used to move the scan data of the upper teeth into proper position the CT scan data.

Figure 10:
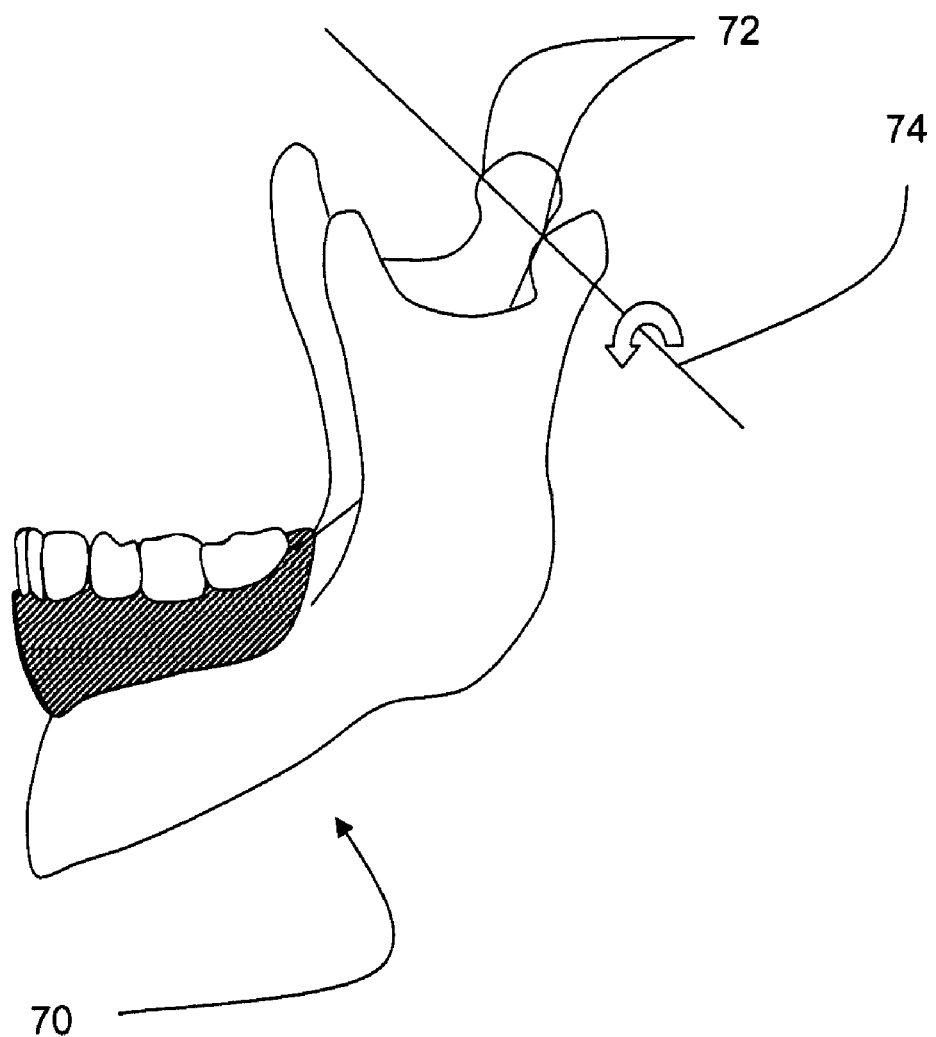
FIG. 10 is a schematic of an exemplary perfected virtual model and the axis of rotation for the lower jaw.

Referring to FIG. 10 the perfected model 70 is illustrated with non-radiographic data from the teeth joined to CT data of the mandible, which was separated from the rest of the scanned data in step 314 of FIG. 3. Points can be selected on or in the area around the articulating surfaces of the condyles 72 to represent the rotational center 74 for the mandible. In a conventional system for determining rotational center, the patient's ear holes are used with a face bow to determine an approximation of the position of the rotational centers. This improved method eliminates the need for a face bow, and the system can determine an approximation for the position of the rotational center. Movement of the mandibular computer model can also be controlled by using standard condylar inclinations and Bennett angles to define average movements.

Figure 11A:
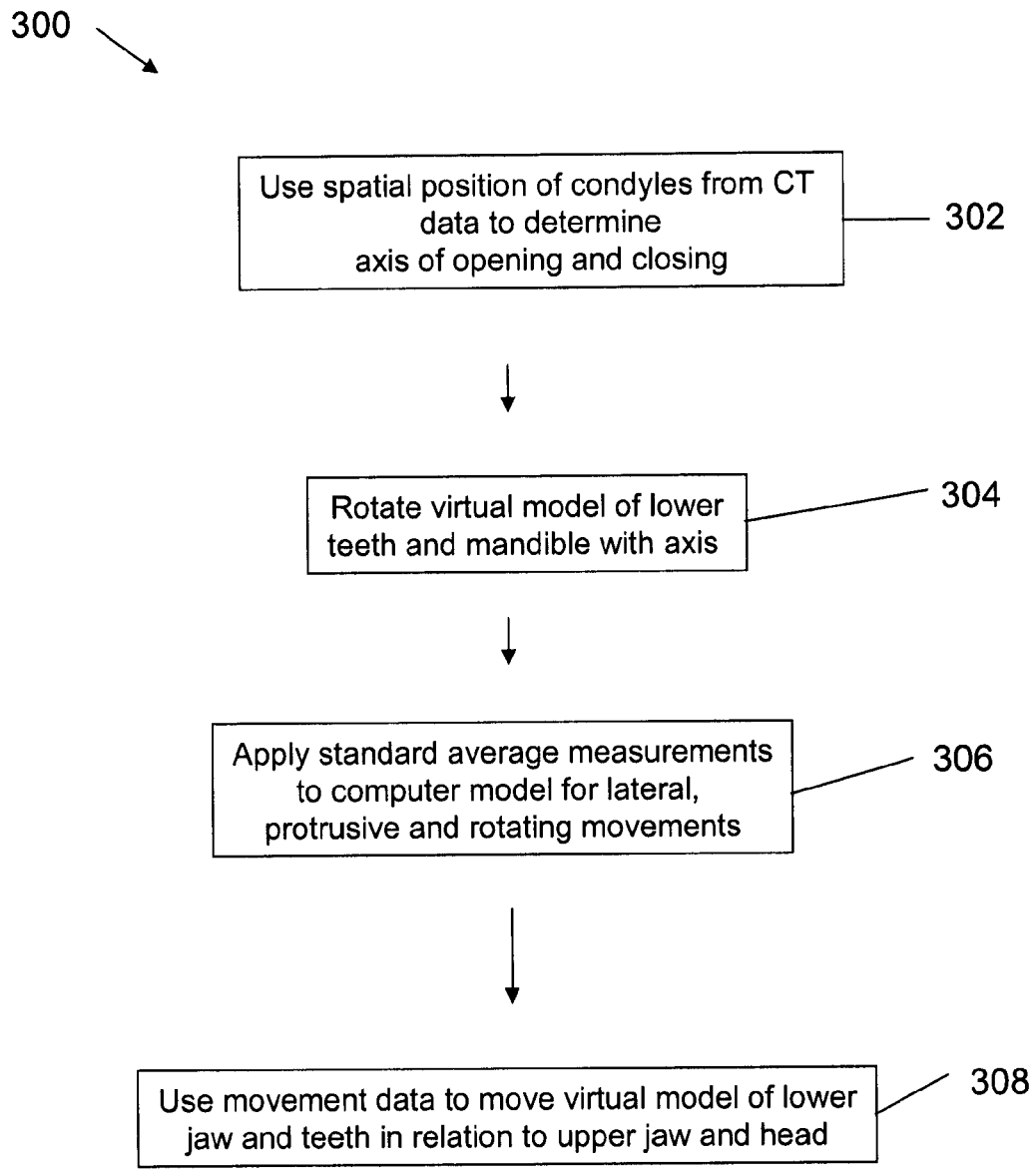
FIGS. 11A and 11B are flow charts showing exemplary processes for creating movement for the lower jaw in a virtual model.
Figure 11B:
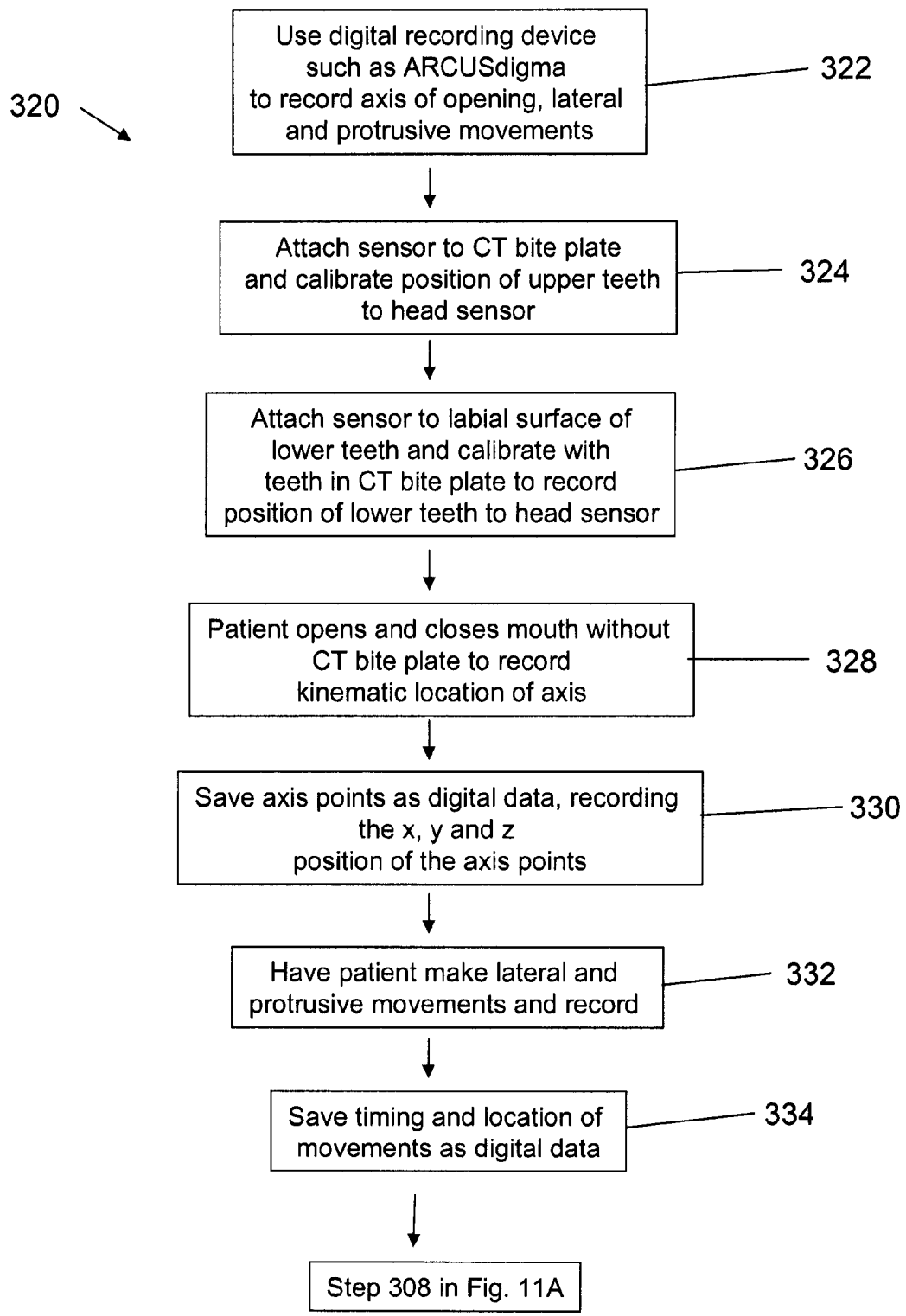

FIGS. 11A and 11B illustrate exemplary processes in a flow chart, referenced herein as 300 and 320 respectively, for applying movement to the mandibular computer model so that the rotational center can be determined.

FIG. 11A begins at a step 302 of using spatial position of condyles from the CT data to determine an axis of opening and closing. This axis may be determined by selecting points on or in the area around the condyles 72 to represent the rotational center 74 for the mandible, as described above with reference to FIG. 10. This may be done with a conventional input device, such as a keyboard, mouse, or other input device. Because the CT data contains all the information for the mandible and condyles, selecting points on or in the area around the condyles 72 may identify the rotational center more accurately than prior art devices relying on the face bow.

At a step 304, a user rotates the virtual model of the lower teeth and the mandible about the axis. Using methods known the art, at a step 306, the user may then apply standard average measurements to computer model for lateral, protrusive and rotating movements to obtain calculated movement data. At a step 308, the obtained movement data is used to move the virtual model of lower jaw and teeth in relation to the upper jaw and head.

In an alternative embodiment, instead of estimating and selecting the rotational axis, the rotational axis is determined through additional scanning steps. One example of this process is shown in and described relative to FIG. 11B. This process may begin at a step 322, where a digital recording device, such as, for example ARCUSdigma, records the axis of opening, lateral, and protrusive movements of the mandible. At a step 324, at least one sensor is associated with the CT bite plate and calibrated to identify the position of the upper teeth relative to a head sensor. This is represented and described with reference to FIG. 12 below.

At a step 326, the sensor attaches to the labial surface of lower teeth and calibrates with teeth in the CT bite plate to record the position of the lower teeth relative to the head sensor. At a step 328, the CT bite plate may be removed, and the patient opens and closes his mouth to record the kinematic location of axis. At a step 330, the axis points are saved as digital data, such as for example, as ASCI Text, thereby recording the x, y and z position of the axis points.

At a step 332, the patient moves the mandible laterally and protrusively, and the relative location, as determined by the sensors, is recorded.

At a step 334, the timing and location of movements are saved or stored as digital data, such as the ASCI Text. Then, as described above with reference to FIG. 11A, the movement data may be used to move the virtual model of the lower jaw and teeth in relation to the upper jaw and the head.

Figure 12:
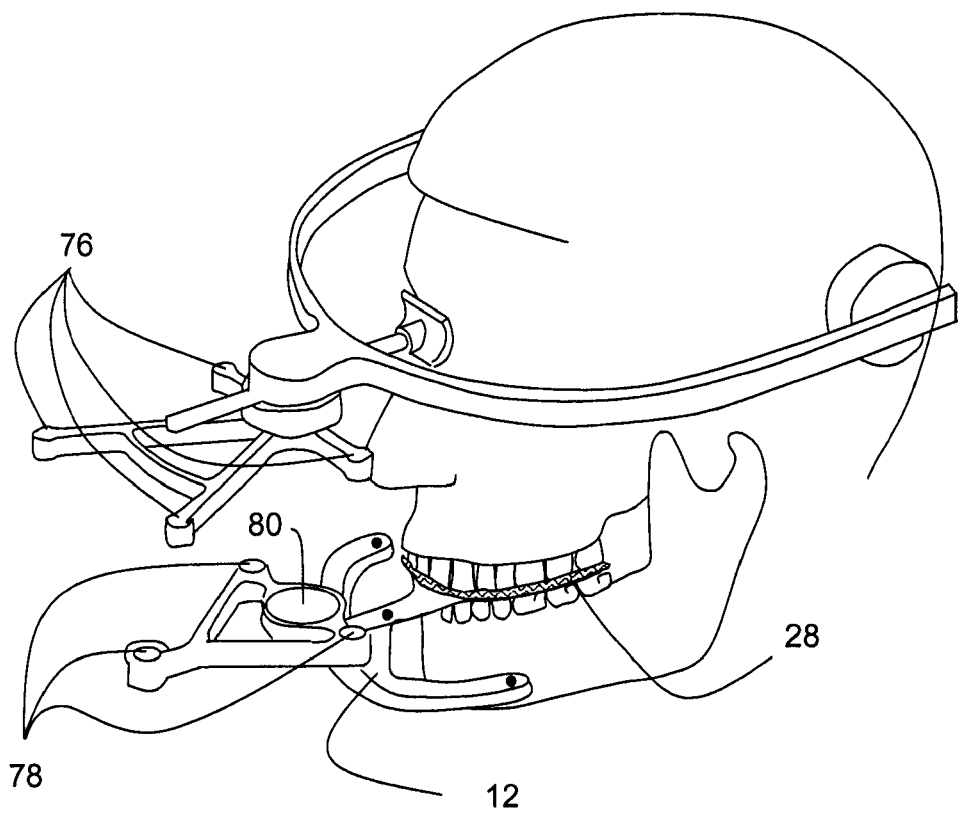
FIG. 12 is a schematic diagram of an exemplary digital recorder attached to the CT bite plate.

FIG. 12 illustrates an exemplary process and system for applying movement to the mandibular computer model. Positional tracking of the patient's physical mandible can be accomplished in many ways that include ultrasound, infrared, light and other methods of recording the positional relationship of the maxillae and mandible to a sensor. The ARCUSdigma (KaVo Company) digital recorder is ideally suited for this task. Four ultrasound microphones 76 are attached to the head and three ultrasonic transmitters 78 are attached to the CT bite plate with a magnetic fixation device 80. The patient bites into the bite registration 28 to reproduce the same positional relationship existed when the CT scan was made. The ARCUSdigma is then calibrated using the operational software. This first calibration records the position of the ultrasonic transmitters 78, CT bite plate 12, and upper teeth in relation to the microphones 76.

Figure 13:
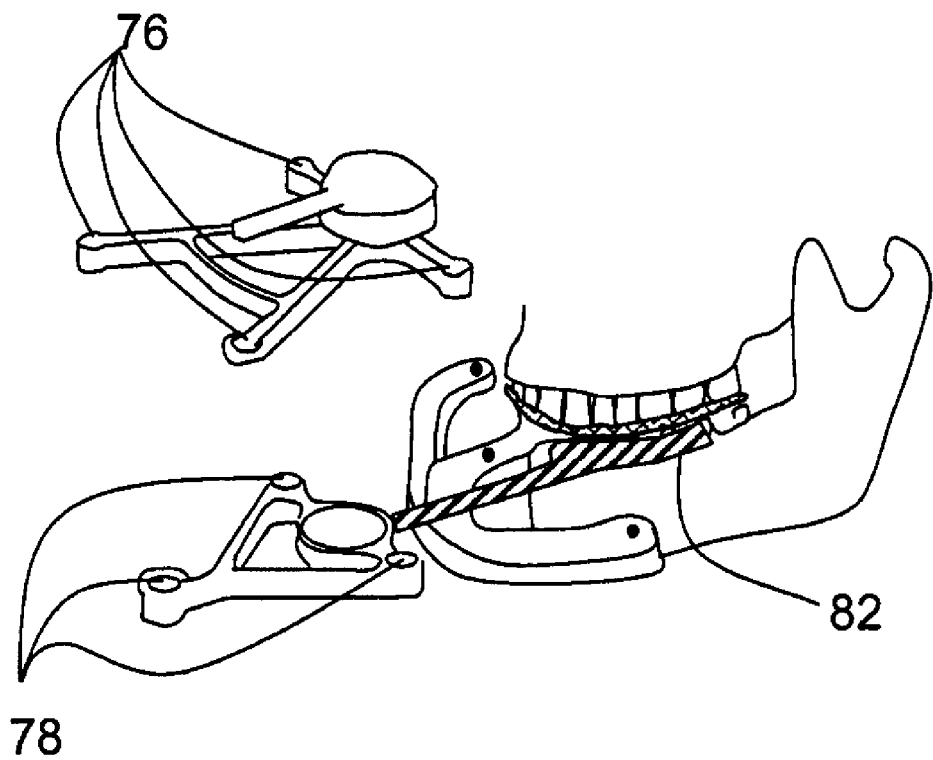
FIG. 13 is a schematic diagram of the exemplary digital recorder attached to the lower bite fork.

FIG. 13 illustrates the lower bite fork 82 attached to the lower teeth such that it is rigidly connected to the teeth and gums and yet below the CT bite plate. The ultrasonic transmitters 78 are then attached to the lower bite fork and the software again is calibrated to record the positional relationship of the lower bite fork and transmitters to the microphones 76 with the patient's teeth in the CT bite plate. The CT bite plate can then be removed to record the motion of the lower jaw to the upper.

Figure 14:
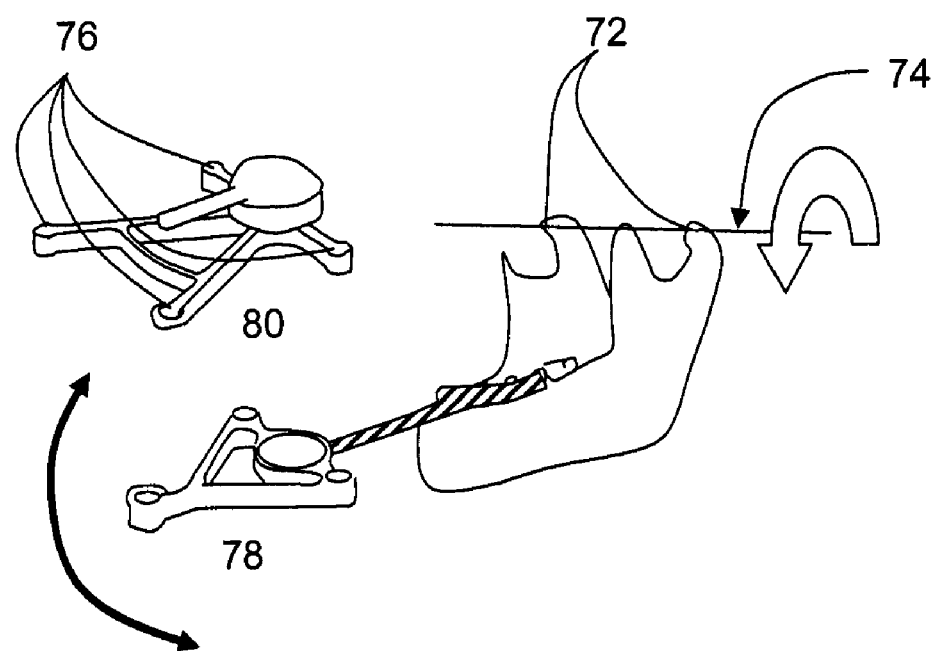
FIG. 14 is an illustration of movement of an exemplary lower jaw to record and locate the axis of rotation of the lower jaw.

FIG. 14 illustrates the process for locating the actual rotational axis of the mandible. The patient's lower jaw is guided in opening and closing positions. The software can then calculate the actual position of the condylar rotational points 72 on the axis of rotation 74. This information is recorded as digital data, such as ASCI Text, and can be directly related to the virtual jaw model described in this invention. The patient can then move in protrusive and right and left lateral jaw movements. The software will record the timing and positional movement of the jaw and record the data as digital data, such as ASCI Text. This text can then be used to move the virtual model of the mandible in computer space.

Figure 15:
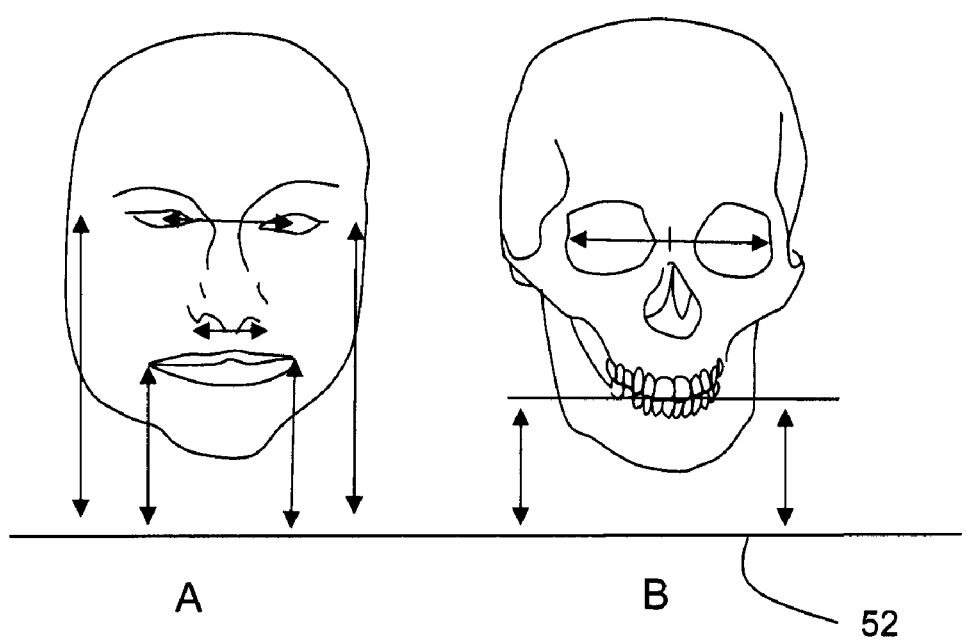
FIGS. 15A and 15B are illustrations of an exemplary virtual model with soft and hard tissues rendered in relation to the horizontal plane.

FIG. 15 illustrates the perfected model used to evaluate the aesthetic position of soft and hard tissues in a natural position, and in relation to the horizontal edge of the sensor 52. Pixels with a grayscale value to render soft tissue (FIG. 15A) can be selected to produce a computer model of the face, nose, ears, and many other structures on the surface of the head. Pixels with a grayscale value for bone and teeth can also be selected to render a computer model (FIG. 15 B) in the same orientation.

Figure 16:
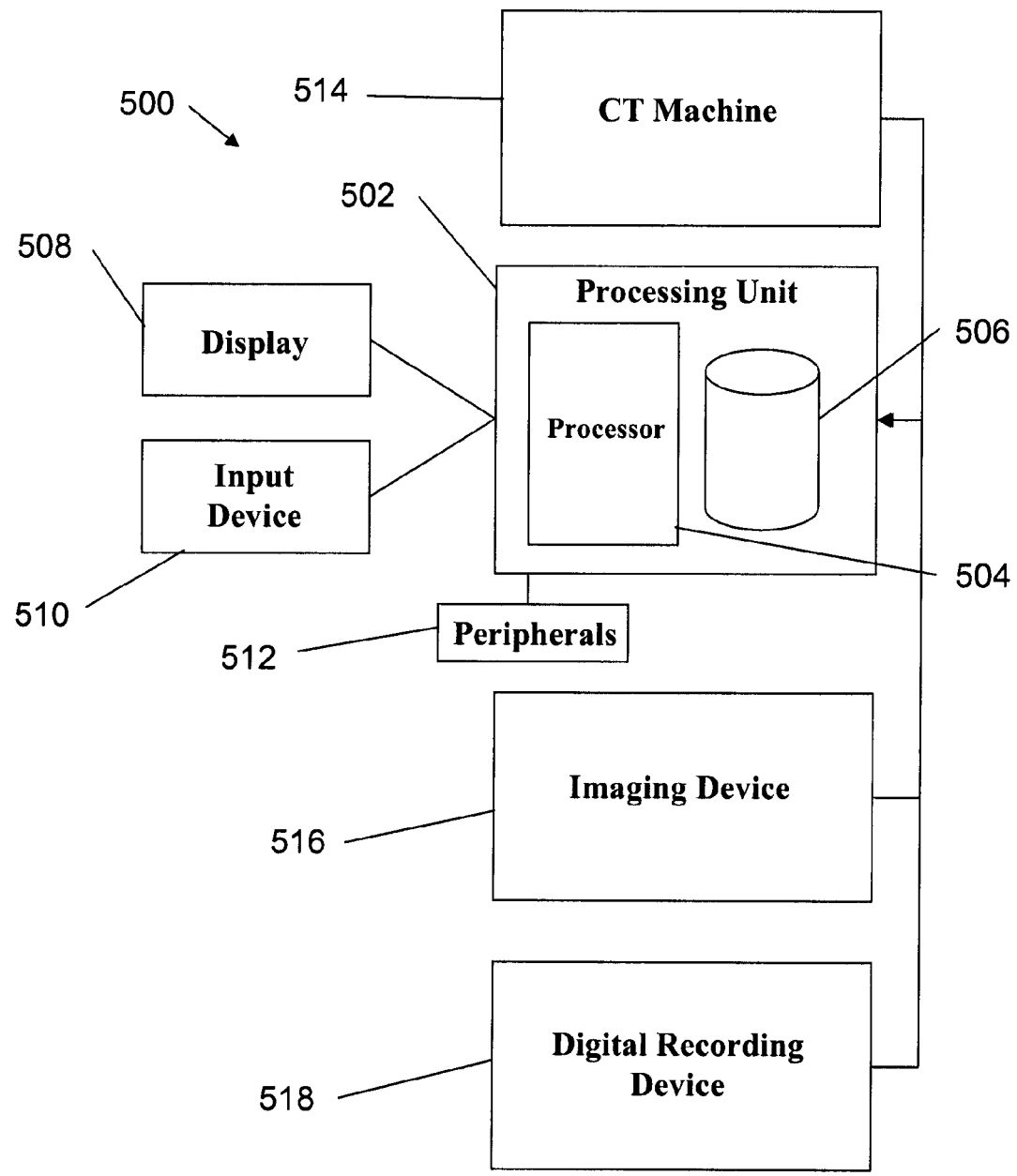
FIG. 16 is a block diagram of an exemplary system usable to accomplish the methods disclosed herein.

An exemplary system for performing the processes and methods described herein is shown in FIG. 16. FIG. 16 includes a computer system 500 including a processing unit 502 containing a processor 504 and a memory 506. An output device, such as a display 508 and input devices 510, such as keyboards, scanners, and others, are in communication with the processing unit 502. Additional peripheral devices 512 also may be present.

The processor 504 may for example be a microprocessor of a known type. The memory 506 may, in some embodiments, collectively represents two or more different types of memory. For example, the memory 506 may include a read only memory (ROM) that stores a program executed by the processor 504, as well as static data for the processor 504. In addition, the memory 506 may include some random access memory (RAM) that is used by the processor 504 to store data that changes dynamically during program execution. The processor 504 and the memory 506 could optionally be implemented as respective portions of a known device that is commonly referred to as a microcontroller. The memory 506 may contain one or more executable programs to carry out the methods contained herein, including joining, separating, storing, and other actions including Boolean actions.

The system 500 also may include a CT machine 514, an imaging device 516, and a digital recorder 518. These may be any of the CT machines, imaging devices, and digital recorders described herein. Data from the CT machine 514, the imaging device 516, and the digital recorder 518 may be accessed by the processing unit 502 and used to carry out the processes and methods disclosed. Data may be communicated to the processing unit 502 by any known method, including by direct communication, by storing and physically delivering, such as using a removable disc, removable drive, or other removable storage device, over e-mail, or using other known transfer systems over a network, such as a LAN or WAN, including over the internet or otherwise. Any data received at the processing unit 502 may be stored in the memory 506 for processing and manipulation by the processor 504. In some embodiments, the memory 506 is a storage database separate from the processor 504. Other systems also are contemplated.

Computer Machined Dental Tooth System and Method

The present invention relates to a dental tooth system that eliminates the steps of cutting, shaping and positioning pre-fabricated denture teeth by hand in the construction of dentures. Digital information from imaging casts of teeth and supporting tissues is joined in computer space to create a virtual model of the patient. Virtual teeth that have the same shape as known pre-fabricated denture teeth are positioned in the computer model and then modified to have the proper form to be joined to the denture base material and to the opposing teeth. The virtual model is used to position the actual pre-fabricated denture teeth in the proper spatial relationship to the dental cast and to cut the occlusal surface of the teeth and the retentive surface of the teeth that will be processed to the denture base material. This system eliminates much of the manual labor and cost of constructing dentures.

Figure 17:
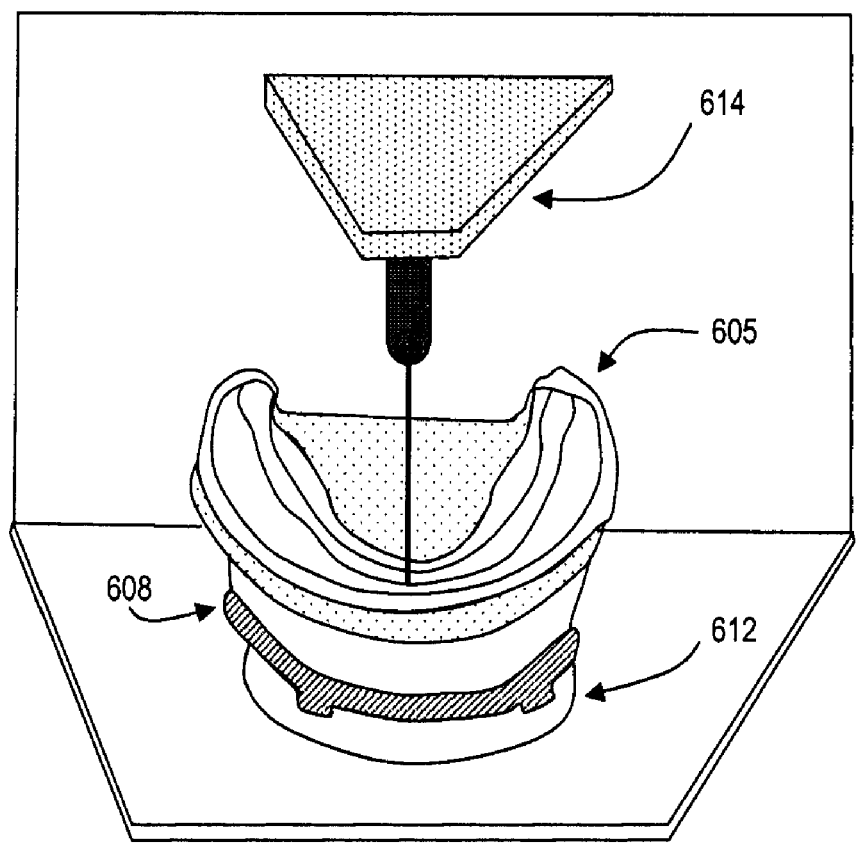
FIG. 17 is a schematic view of an exemplary lower edentulous cast attached to an exemplary mounting plate receiver in a digital 3D scanner.

Turning now the figures, FIG. 17 illustrates an edentulous lower cast 605 joined to a mounting plate 608 seated in a mounting plate receiver 612. The cast is positioned in a digital imaging system 614. The imaging system 14 may be contact imaging system, or may be a light, laser, radiographic, holographic, or other suitable imaging system. The imaging system 614 creates a data set of the 3D surface of the dental cast in a known spatial relationship to the mounting plate receiver 612. The data can be stored in computer memory as a text file recording specific x, y and, z points in relation to the mounting plate receiver or the points can be altered to produce a mathematical surface or solid model of the dental cast using mathematical algorithms known in the imaging art. In one exemplary embodiment, the surface image of the dental cast is saved as a .stl (stereolithography) file which records the surface as a series of small triangles. The upper dental cast is imaged in the same manner to create a data set for the surface of the upper cast in relation to the mounting plate receiver.

Figure 18:
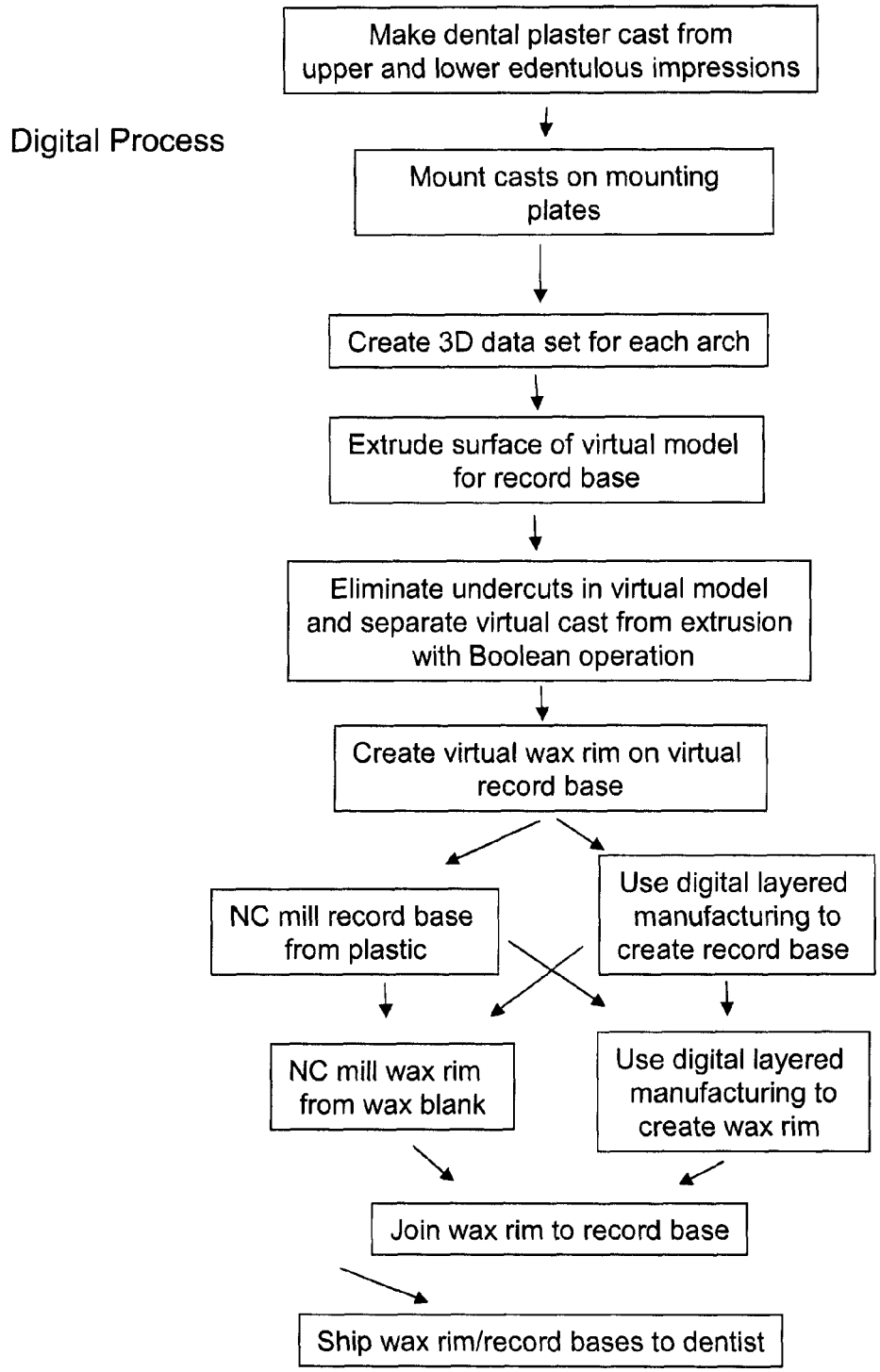
FIG. 18 is a flow chart showing one exemplary method of manufacturing a wax rim and a record base using digital methods.

FIG. 18 is a flow chart showing the process of making the record base and wax rim using exemplary embodiment of digital techniques embodied in this disclosure. In some embodiments, the .stl file of the dental cast is extruded to create, for example, a 1-2 mm offset to the virtual cast. Undercuts in the virtual model also maybe eliminated. Boolean operations may then be used to separate the dental cast data from the extruded object. The extruded object is saved as a separate .stl file for manufacturing the record base. The record base can be manufactured with, for example, layered manufacturing such as stereolithography or any of a number of digital additive manufacturing systems that will make a plastic object from a .stl file. In some embodiments, the record base can also be manufactured from a blank of plastic material using machining processes, such as, for example, a process performed with number controlled milling. For machining, such as when milling, the .stl file may be converted to numeric code to control, for example, a four of five axis mill to cut the record base. The wax rim also may be designed as a digital 3D file of the planned shape needed for the dentist. The wax rim, like the record base, may be manufactured using any suitable method, including using layered manufacturing and machining, including milling. Reference points on the virtual cast may be used to create the form of the wax rim. Some examples of references points are the retromolar pad and the labial sulcus. These reference points are well known in the dental art and are used by dental technicians to make wax rims using the traditional hand process. The form of the virtual wax rim is also saved as a .stl file and can be used to manufacture the wax form with layered manufacturing or number controlled milling. Once the wax rim and record base have been manufactured they can be joined together and shipped to the dentist to try in the patient's mouth. An upper or lower cast can be used with this process. While the example described above employs a digital process, in some exemplary embodiments, traditional processing can be used, including blocking-out undercuts with wax and making the record base with acrylic resin or a light cured composite. The wax rim can be formed by manually adding wax to the record base using anatomic landmarks.

Figure 19:
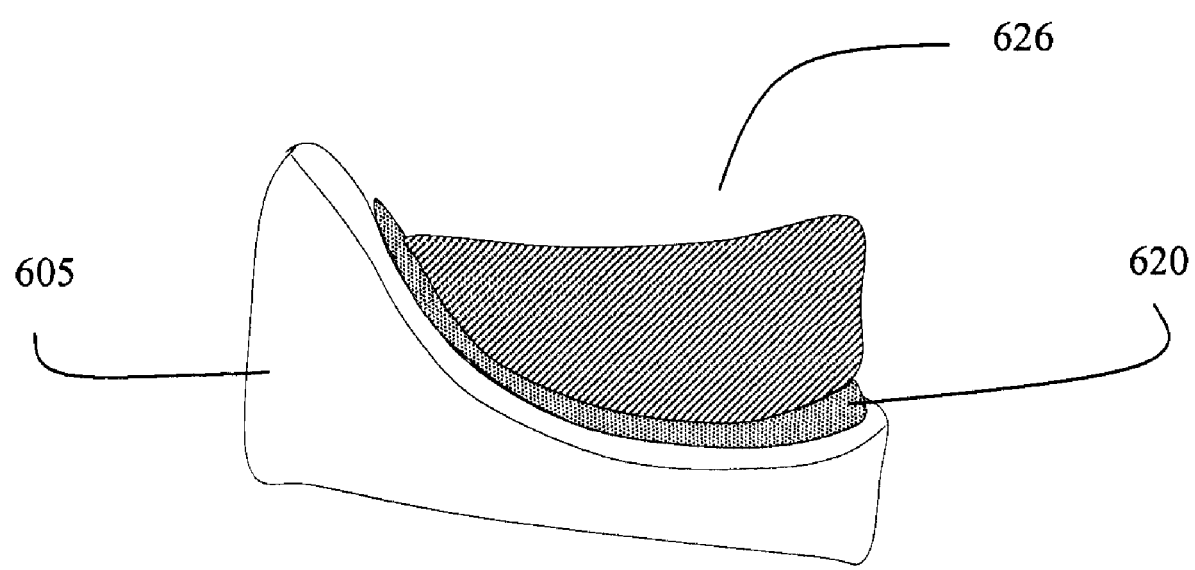
FIG. 19 is an illustration of an exemplary dental cast, record base, and wax rim.

FIG. 19 shows one example of the lower edentulous cast 605, record base 620, and the wax rim 626. The upper and lower wax rim and record base may then used by the dentist to evaluate the shape, aesthetics and bite relationship of the record base and wax rim in the patient's mouth. Any changes that are required may be made in the wax by the dentist. The dentist also may makes a centric bite record of the spatial relationship of the upper and lower jaws using the wax rims and record bases. The centric bite record and record bases are then sent to be imaged again and to have pre-fabricated denture teeth positioned properly in the wax rim.

Figure 20:
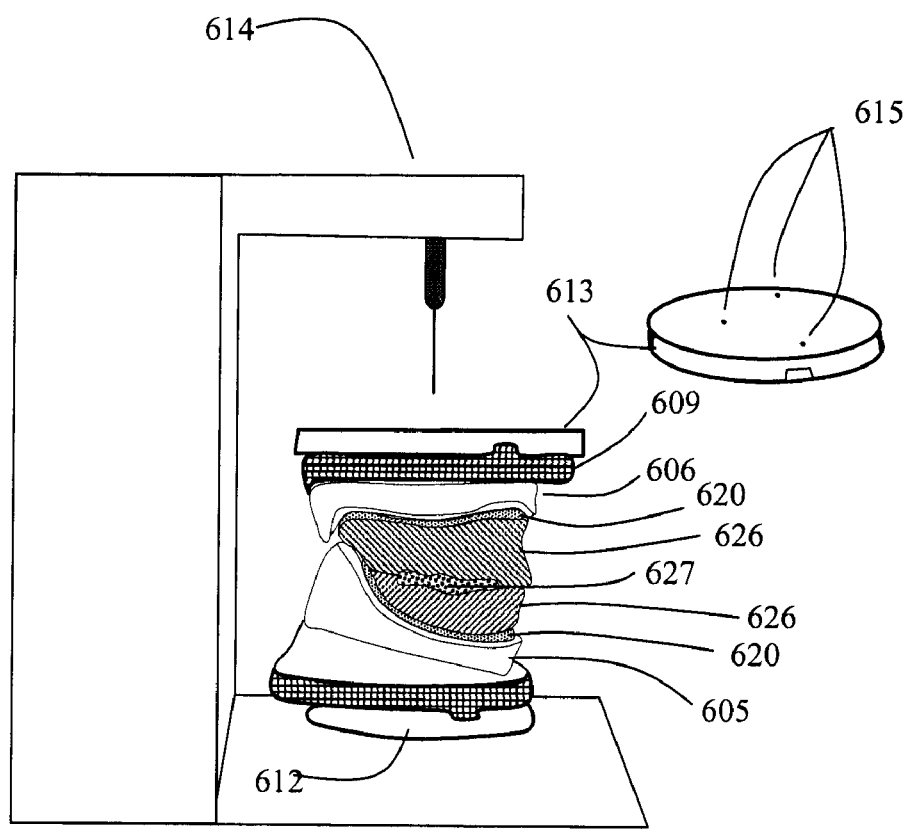
FIG. 20 is an illustration depicting the exemplary upper and lower casts, record bases, centric bite record, and wax rims on an exemplary digital scanner with an exemplary calibrating mounting plate receiver attached to the upper mounting plate.

Turning now to FIG. 20 of the drawings, there is depicted the exemplary upper 606 and lower 605 cast, record bases 620 and wax rims 626 on the exemplary digital scanner 614. The lower cast is shown seated in the mounting plate receiver 612 and the upper cast is held in position with a centric bite record 627, obtained from the dentist. The bite record was made by the dentist and it records the correct orientation of the upper cast to the lower for construction of the dentures. A calibrating mounting plate receiver 613 is attached to the upper mounting plate 609. In FIG. 20, two images of the mounting plate receiver are shown for reference. The calibrating mounting plate receiver 613 may be used to record the spatial orientation of the upper mounting plate to the scanner and its mounting plate receiver 612. In this exemplary embodiment, the calibrating mounting plate receiver 613 has three small indentations 615 on its surface that can be detected with the scanner and are used to move the upper cast scan data in computer space using a three point move (CADKEY® Baystate Technologies Inc.). This will position scan data about the upper cast 606 and wax rims 626 in the same orientation in the virtual model as exists in the patient's mouth. Any additional scans of the upper cast, wax rim, or denture teeth can then be moved in the virtual model to the same orientation as existed with the bite record 627. Next the upper and lower casts 605, 606 and wax rims 626 may be scanned to determine the shape of the rims after the dentist modified them with the patient. The reshaped wax rim 626 may indicate information such as, for example, the midline, position of anterior teeth and the occlusal plane. This information along with other virtual anatomic reference points may be used to position virtual denture teeth with a shape identical to the actual manufactured denture teeth in the computer model.

Figure 21:
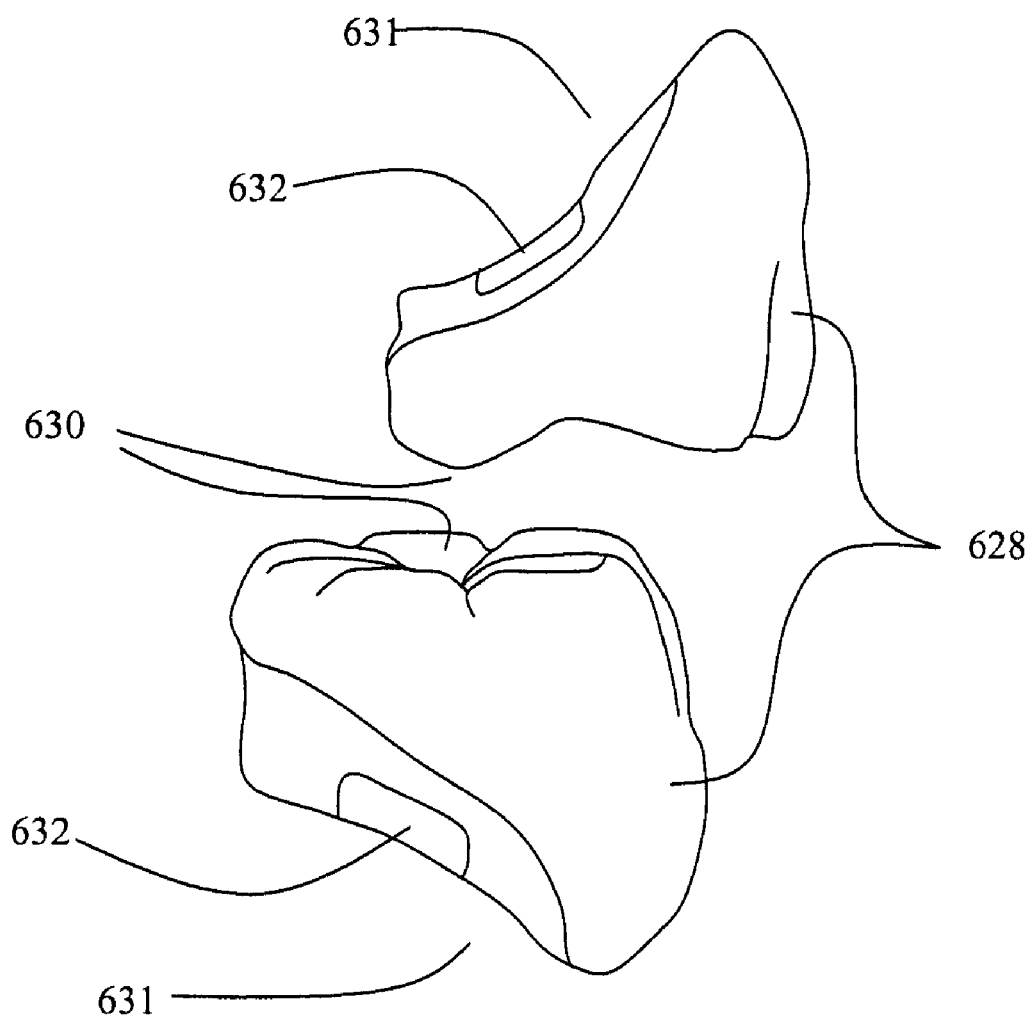
FIG. 21 is an illustration depicting a side elevation view of exemplary posterior teeth, illustrating the aesthetic outer surface, the occlusal biting surface, and the surface directed toward the residual ridge with retentive undercuts.

Referring to FIG. 21 of the drawings, pre-fabricated denture teeth have an outer aesthetic surface 628 that is oriented toward the cheeks or lips; this surface is visible to other people that are looking at the patient. This surface is generally not changed in the process of positioning denture teeth and making dentures because it has an ideal pre-formed aesthetic form. The occlusal biting surface 630 of the denture tooth is oriented toward the opposing arch and in conventional methods is frequently ground by hand to create proper contact with the opposing denture teeth during function. The surface 631 directed toward the residual ridge is frequently ground extensively to accommodate the form of the residual ridge and implant components. As the surface is ground away, the retentive features in the denture tooth 632 are also removed.

Figures 22, 22A, 22B:
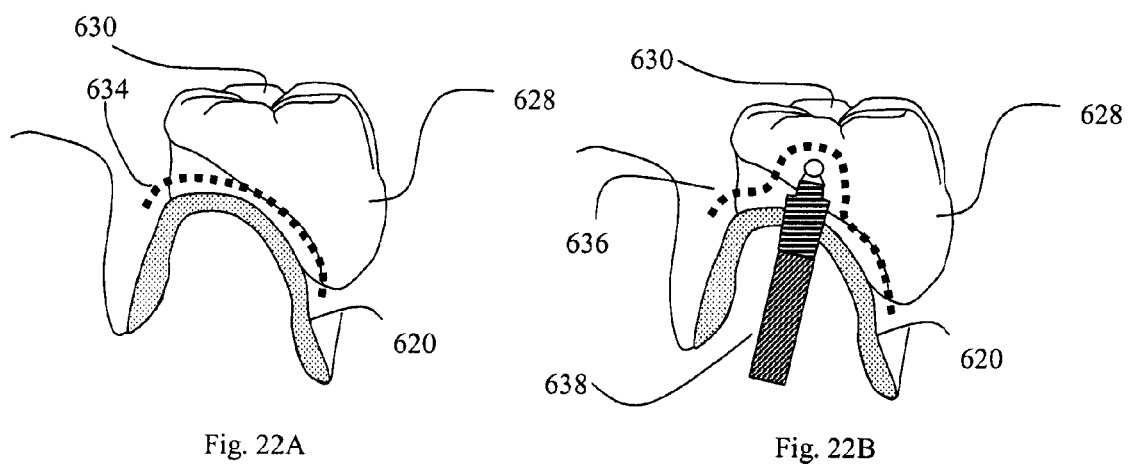
FIG. 22 A is an illustration of an exemplary artificial tooth in relation to the residual alveolar ridge.

Now referring to FIG. 22A as the surface directed toward the residual ridge and record base 620 is ground away, as shown by the dashed line 634, the retentive features are also removed. This can cause the denture tooth to become less retentive in the denture base material unless the retentive features are reground into the tooth. Space also may be created for implant components if the denture is stabilized with implants. FIG. 22B illustrates the area that must be ground away 636 for the implant components 638. FIGS. 21 and 22 illustrate a lower molar, although any pre-fabricated denture tooth is modified in this way.

Figure 23:
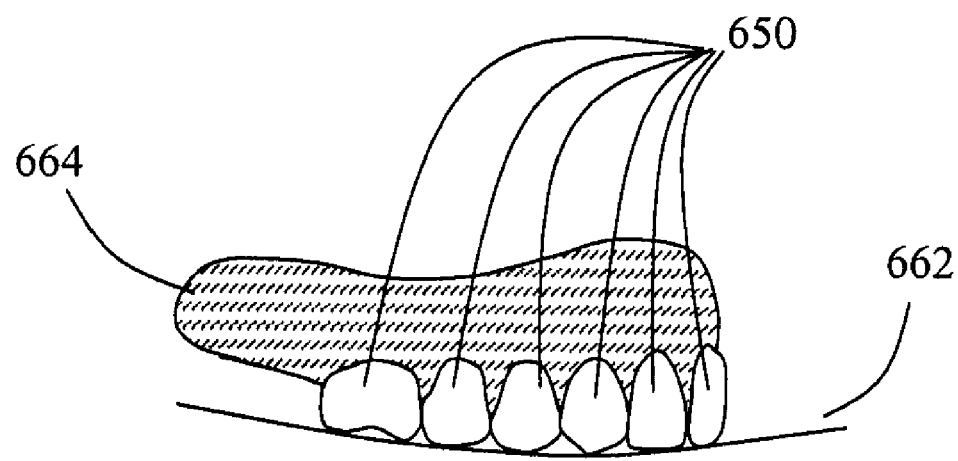
FIG. 23 is a schematic of exemplary upper virtual denture teeth in relation to an exemplary virtual reference plane and the virtual wax rim.

Dentures are constructed from pre-fabricated denture teeth and each tooth has a specific form and color. The form of the teeth is generally indicated by a mold number and each manufacturer maintains consistent manufacturing practices to insure that the teeth are always the same size and form. Now referring to FIG. 23, virtual upper denture teeth 650 are illustrated in proper spatial relationship to the virtual reference plane 662 and the virtual wax rim 664. In some embodiments, the data set for each virtual tooth 650 is made by scanning the actual pre-fabricated denture tooth and saving the scan data in a 3D file format. The scanning may be accomplished using any known scanning system, including those types identified herein. Alternatively, the data set may simply be provided by the tooth manufacturer or may otherwise be obtained. There are many 3D file formats in the imaging art and the .stl format is a common one. The virtual teeth are moved in computer space to align with the virtual image of the wax rim 664, reference plane 662 and record base, as shown in FIG. 23. Computer software such as FREEFORM™ (SensAble Technologies Inc.) can easily move and modify 3D data in the .stl file format. The virtual reference plane 662 may be a flat virtual plane for monoplane tooth set-up or alternatively, a section of a sphere for setting the teeth to a curve. Since the reference plane 662 is virtual, any number of shapes can be used, providing the operator with multiple options. The disclosed methods are much improved over conventional methods since the virtual teeth can overlap other objects in computer space during the positioning process. In conventional methods, the dental technician hand grinds each tooth and fits it to the residual ridge and opposing tooth before moving on to the next tooth. Using a virtual model, all the teeth can be positioned ideally as shown in FIG. 23, and then cut to fit using Boolean operations in the computer software. Once the virtual teeth have been positioned in the correct relationship to the residual ridge and opposing teeth, a Boolean operation is used to cut the surface of the virtual teeth such that a space exists between the teeth and the residual ridge or implant components. The cut surface of the denture teeth may be saved as a .stl file for later conversion to numeric code to mill the actual denture teeth. The same process may be used to set and shape the lower virtual denture teeth. This virtual tooth set-up can then be sent to the dentist via the Internet (SolidView—Solid Concepts, Inc.) to evaluate the shape and position of the teeth. Several free .stl viewer programs are available for viewing 3D computer data. If the virtual set-up is acceptable to the dentist and/or the patient, then the actual denture teeth may be positioned in the same orientation using techniques revealed in this disclosure below.

Figure 24A:
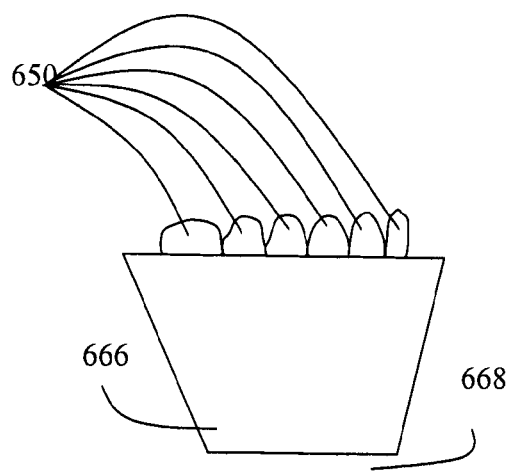
FIG. 24 A is a schematic of the exemplary virtual denture teeth in relation to an exemplary virtual positioning block in computer space.
Figure 24B:
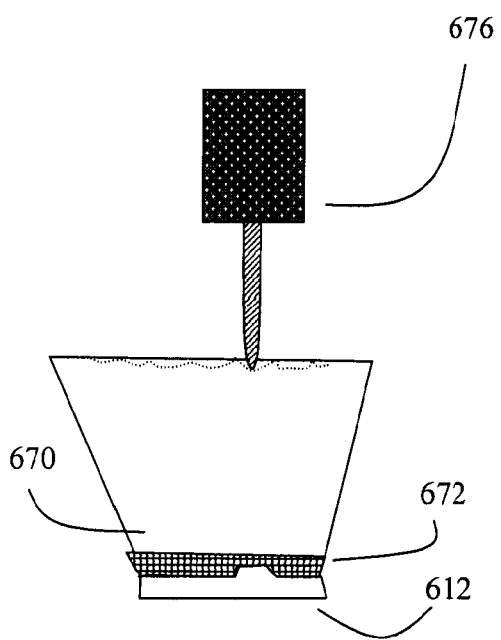

FIG. 24A illustrates a virtual positioning block 666 made in computer space that covers the occlusal or biting surfaces of the upper virtual denture teeth 650. The positioning block 66 is made in a known x; y, and z orientation 668 in computer space that reproduces the spatial orientation of the upper cast recorded with the centric bite record 627 and calibrating mounting plate receiver 613. A Boolean operation may then be used to cut the shape of the virtual denture teeth 650 from the surface of the virtual positioning block 666. This will leave indentations in the block 666 that are the negative shape of the denture teeth. The indentations are generally 1-2 millimeters deep. The 3D data set of the virtual positioning block 666 is then saved as a .stl file and the upper surface of the .stl file is translated into numeric code to machine, such as using a mill, the same shape from an actual block of material such as plaster. Computer software such as DeskProto from Delft Spline Systems can easily translate .stl surfaces to numeric code. FIG. 24B is a schematic diagram of the actual plaster positioning block 670 attached to a mounting plate 672 which is seated in a mounting plate receiver 612 attached to a machining device, which in this example is a number controlled mill 676. The mill 676 is used to cut the surface of the plaster 670 to create indentations that are the negative shape of the actual denture teeth, as determined in the virtual model.

Figure 25:
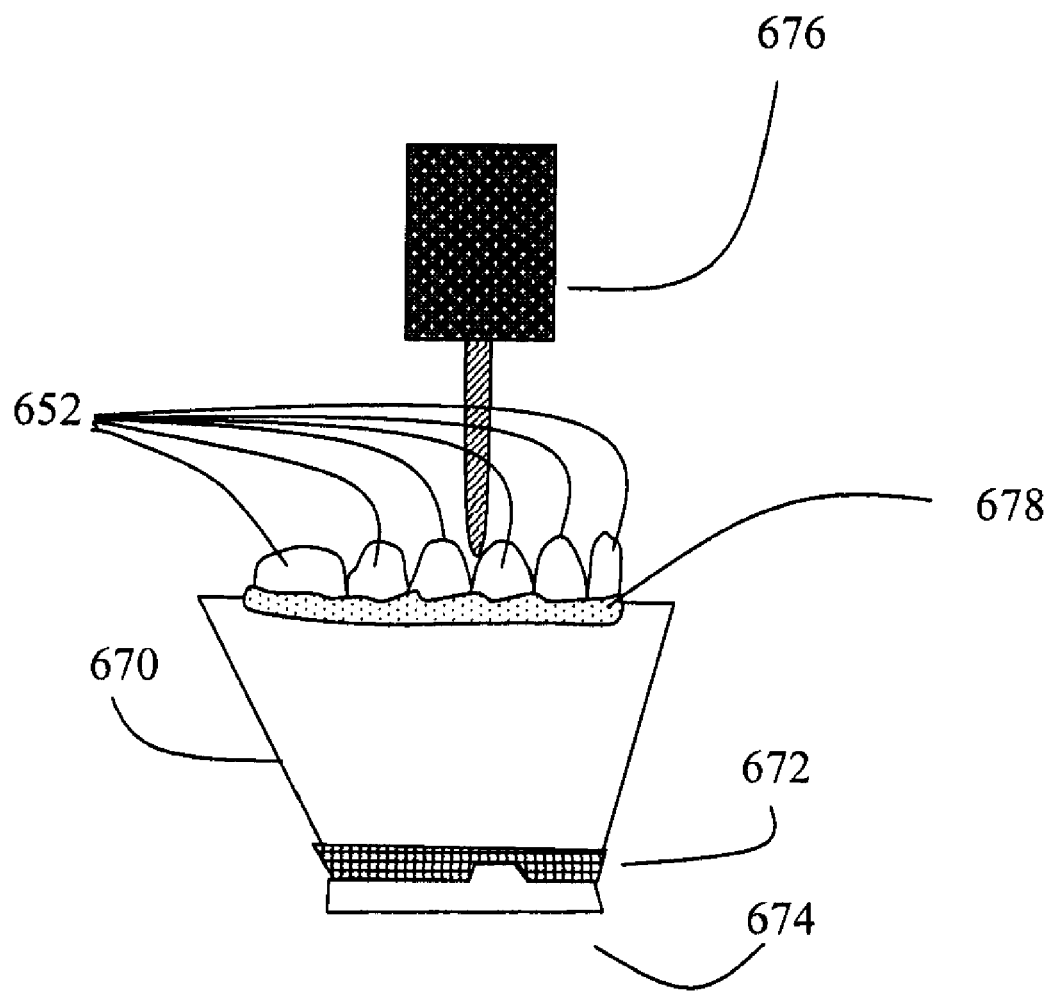
FIG. 25 is a schematic of exemplary actual pre-manufactured denture teeth attached to the plaster reference block with adhesive and being milled.

Once the actual positioning block 670 is prepared, the actual pre-manufactured denture teeth 652 may be introduced into the indentations. FIG. 25 shows a diagram of the actual pre-manufactured denture teeth 652 positioned in the plaster positioning block 670 and held in place with a temporary adhesive 678. This is very simple task for a laboratory technician, since the correct position of each tooth has already been determined from the shape of the indentations in the plaster block.

Figure 26:
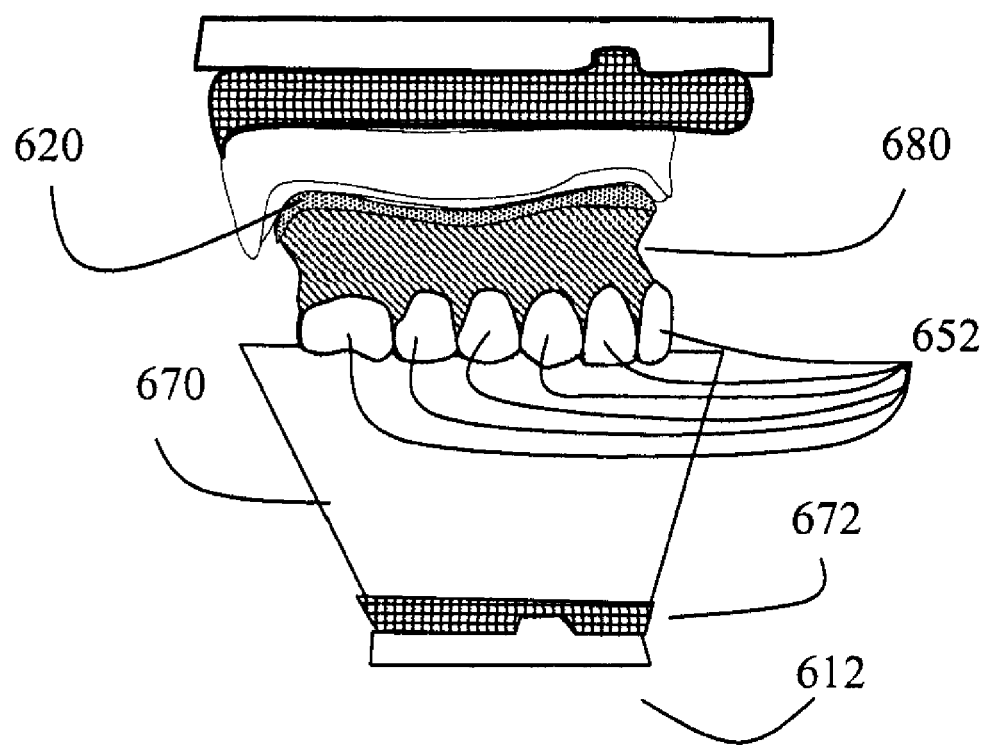
FIG. 26 is an illustration depicting the actual denture teeth joined to the wax rim and record base.

Next the surfaces of the denture teeth 652 facing the residual ridge or implant components are cut by machining, such as with a mill 676. The .stl file of the cut surface of the virtual teeth is converted to numeric code to cut the actual teeth in the same shape as the virtual ones. The surface of the virtual teeth to be cut was discussed above, with reference to FIG. 23. After the surface of the denture teeth facing the residual ridge has been milled, the positioning block 670 may be positioned in the same relation to the upper cast as was determined from the bite record 627 (FIG. 20), as is shown in FIG. 26. The space (discussed above during the virtual cutting discussion with reference to FIG. 23) between the actual denture teeth and the record base is filled with wax 680 to create a try-in suitable for placement in a patient's mouth for fitting purposes. This may embed and orient the teeth in the wax in the substantially identical position as the teeth in the virtual image. Once secured in the wax, the teeth may be lifted or otherwise removed from the positioning block 670.

In some exemplary embodiments, placement of the actual pre-manufacture denture teeth 652 are placed within the indentations in the positioning block 670 using an automated system, such as a robot system. In some of these embodiments, the robot may select the teeth based on the virtual images, retrieve and orient them, and place them in the positioning block with the occlusal or biting surfaces embedded in the block, matching the virtual image. In some embodiments, the actual denture teeth may be made or modified such that extensions or unique shapes are made that allow for precise positioning of the teeth in the positioning block using a robot system. This can be accomplished using a robotic system to pick up each specific tooth and to position it in a specific position determined from the virtual positioning of the virtual denture teeth.

Figure 27:
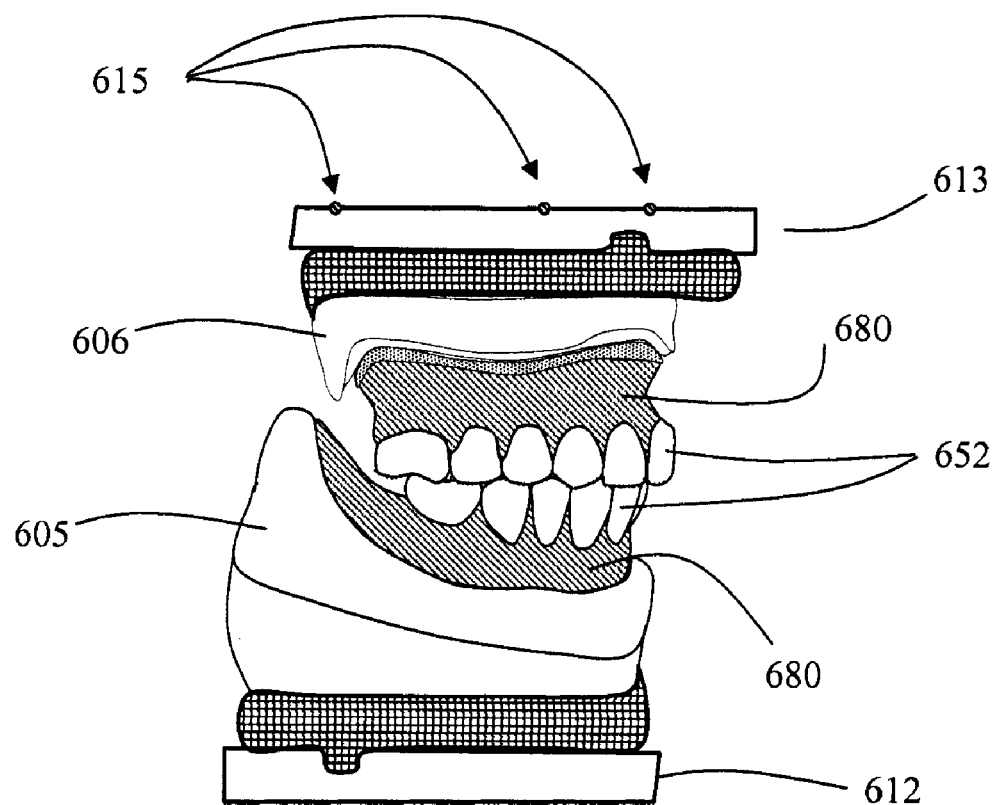
FIG. 27 is a schematic of the exemplary actual denture teeth set in wax ready for try-in by the dentist.

The process used on the upper denture teeth may be used to mill and position the lower denture teeth. FIG. 27 illustrates a try-in of the actual upper and lower denture teeth 652 set in wax 680 according to one exemplary embodiment of this disclosure. Note that the upper and lower casts 606, 605, are in the same spatial orientation as existed when they were imaged with the centric bite record in FIG. 20. Note also that the referencing points 615 are also in the same orientation. The wax try-in set-up, with the teeth, is then sent to the dentist to try in the patient's mouth to validate the proper position of the teeth and to make static records of the patient's jaw movement. Static records are a common method of approximating the positional orientation of the upper jaw in relation to the lower jaw. Normally one or more of protrusive, left, and right lateral static records are made. The protrusive record may be made with the patient's lower jaw moving forward until the upper and lower front teeth are in an end to end relationship. A recording material such as wax is placed between the denture teeth to record the positional relationship of the upper denture to the lower. Accordingly, the position of the upper denture can be measured against the opposing elements, such as the lower denture (or alternatively actual teeth), and/or the position of the lower denture can be measured against the opposing elements, such as the upper denture (or actual teeth). These static records allow duplication of the patient's jaw position and movements in the lab.

Figure 28:
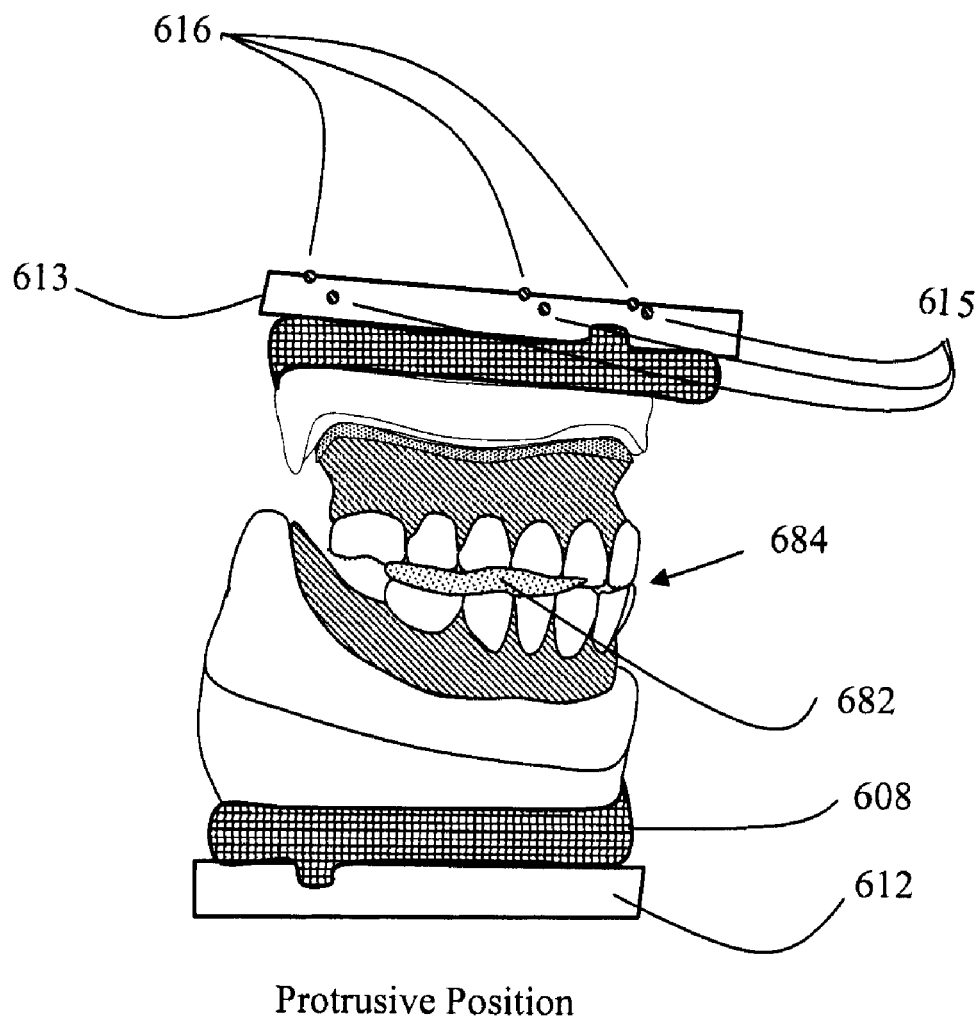
FIG. 28 is an illustration of the exemplary upper and lower denture tooth wax-ups with an exemplary static protrusive record between the teeth to record the change in position of the upper cast.

FIG. 28 illustrates the protrusive bite record 682 and the position of the upper and lower teeth 684 on the mounting plate receiver 612. Now referring to the calibrating mounting plate receiver 613, note that the position of the three referencing points 615 have changed to new positions 616 with the static bite record in place, and each new point position can be recorded as an x, y, and z coordinate in relation to the lower mounting plate receiver 612. After the position of the protrusive record has been made, the right lateral and left lateral records also may be placed between the teeth and the position of each reference point recorded again. In some exemplary embodiments, a total of 612 points are recorded, three for the centric position, three for the protrusive position and three for the right and the left lateral position. Since three points can determine the position of any object in computer space, the position of the virtual upper denture can be moved using each set of three points for the centric, protrusive, right lateral and left lateral position of the upper denture and teeth.

Figure 29:
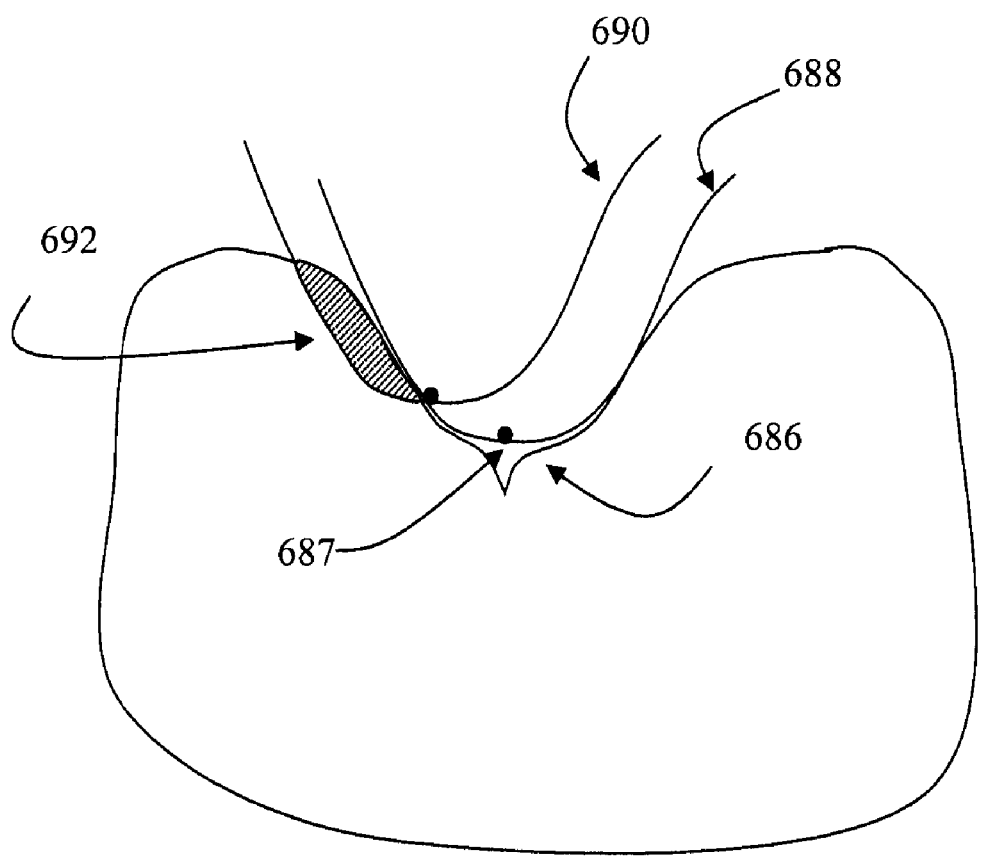
FIG. 29 is an illustration of a lateral (buccal) view of an exemplary lower molar denture tooth fossae and opposing upper lingual denture tooth cusp.

FIG. 29 illustrates a lateral (buccal) view of a lower molar denture tooth fossae 686 and the opposing upper lingual denture tooth cusp 687. The position of the cusp 687 in centric relation position 688 and protrusive position 690 is illustrated. Note that an area of the lower molar is an interference 692 and in a conventional process, this area is frequently ground by hand to create "balance' in the denture.

Figure 30:
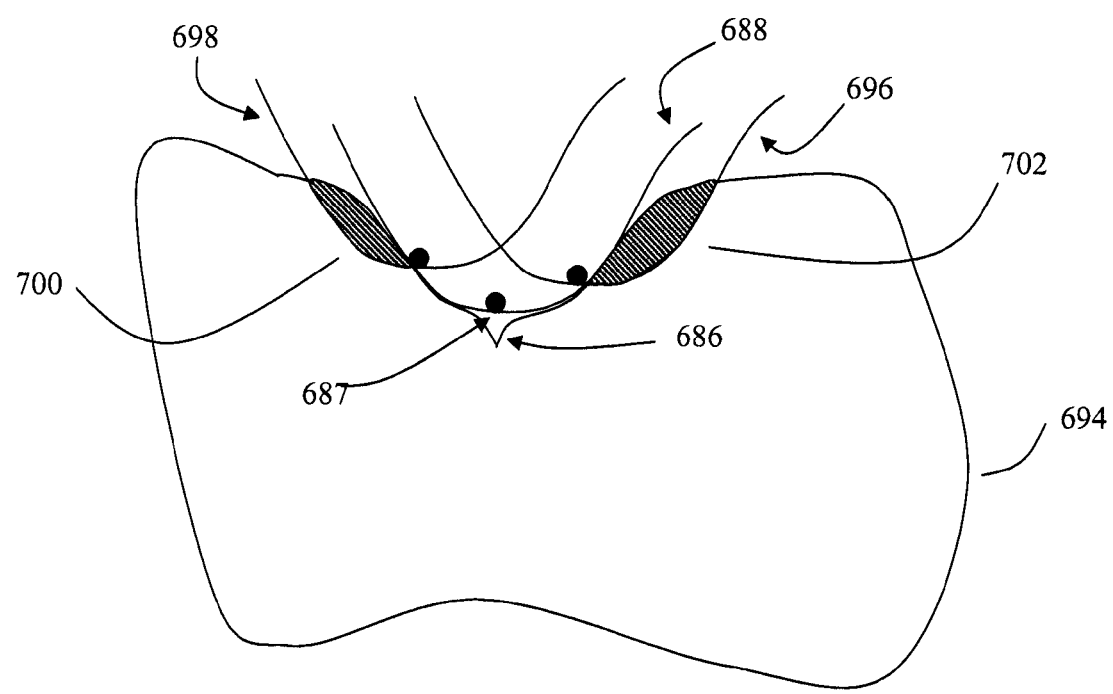
FIG. 30 is an illustration of a frontal view an exemplary lower left molar tooth illustrating the central fossea and the opposing lingual cusp.

FIG. 30 is a frontal view the lower left molar tooth 694 illustrating the central fossea 686 and the opposing lingual cusp 687. The position of the upper cusp in a right lateral position is indicated by the reference numeral 696 and the position of the upper cusp in a left lateral position is indicated by the reference numeral 698. Note the area of interference 700 that occurs when the molar is in the left lateral position. This area of interference 700 is also called a working interference in the dental art. Now referring to the right lateral position 696, note the area of interference 702, this area of interference is called a balancing interference. In a conventional process, these areas of interference were ground by hand to reduce the lateral forces on the denture and to maintain stability.

Figure 31:
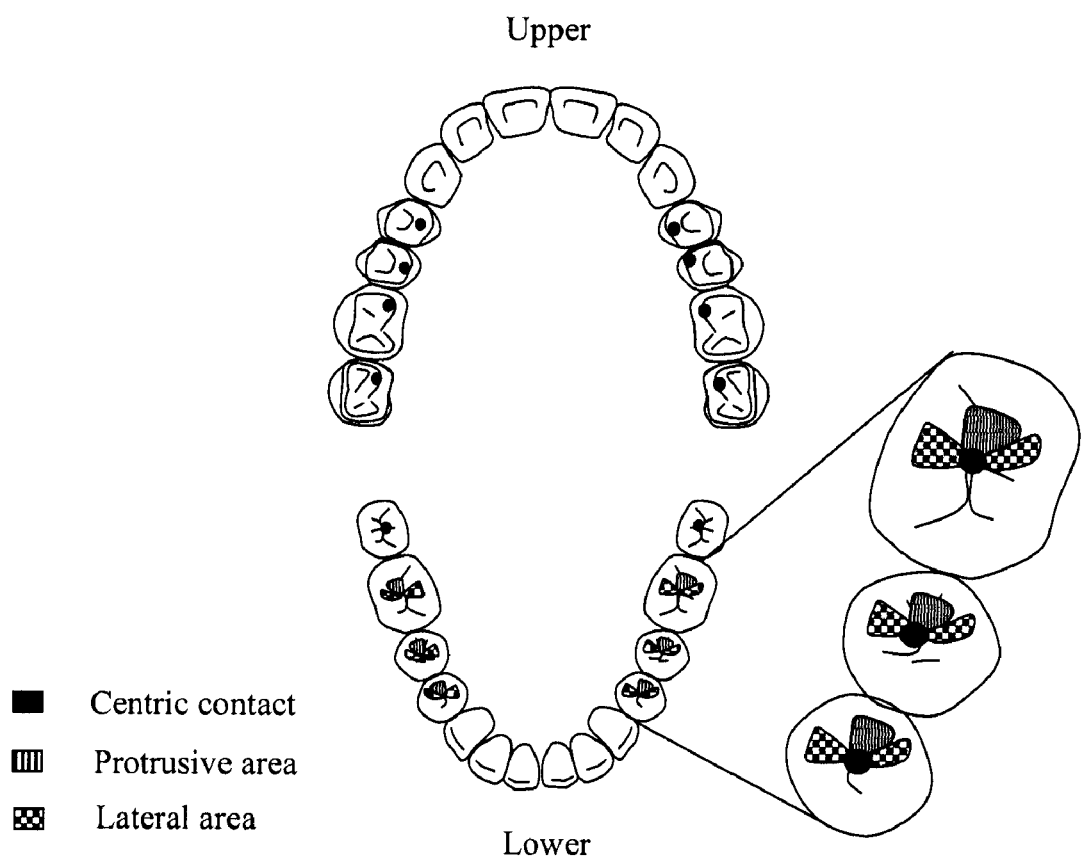
FIG. 31 is an illustration of upper and lower biting surfaces of exemplary denture teeth.

Now referring to FIG. 31, the upper and lower biting surfaces of the upper and lower virtual denture teeth are illustrated. The upper denture teeth have the same three dimensional form as the original design, as shown in FIG. 23. The virtual model of the upper denture has been moved in computer space using the three point move process common to computer aided design software such as CADKEY® (Baystate Technologies Inc.). The upper virtual model can be positioned in centric, right lateral, left lateral and protrusive positions and all positions in between. The area marked protrusive is the area removed from the lower teeth from centric relation position to the protrusive position to reduce or eliminate interference. The area marked lateral area is the area removed from the centric to the right and left lateral position to reduce or eliminate interference. Boolean operations are used to remove material from the lower virtual denture teeth. Illustrated in the preferred embodiment is a balanced type of occlusion but any type of denture tooth or concept of denture occlusion can be created with this virtual design process. By selectively removing virtual material from the lower teeth it is possible to create "bilateral balance" in the denture without occlusal interferences. Static centric, right lateral, left lateral and protrusive records are described in the disclosed embodiments of this disclosure, but other methods of tracking of the mandible can be used also and they include, for example: ultrasound, infrared, light, averaged measurements to record the positional relationship of the maxillae to the mandible, and other suitable methods. The ARCUSdigma (KaVo Company) digital recorder is ideally suited for this task. This recorder employs four ultrasound microphones attached to the head and three ultrasonic transmitters attached to the lower record base. The positional movement and timing of the movement of the jaw is saved as z, y, and z coordinates in ASCI text and can be used to create movement of the virtual computer model, enabling interference recognition and bilateral balancing of the upper and lower dentures.

After using the wax try-in models returned from the dentist to digitally record the protrusive and/or lateral records, the models are processed to generate the final dentures. Processing includes removing the wax and record base from the teeth and fixing them in a suitable denture base material to secure them in place relative to each other. This may be done using, for example, a heat or autopolymerizing denture base material.

Figure 32:
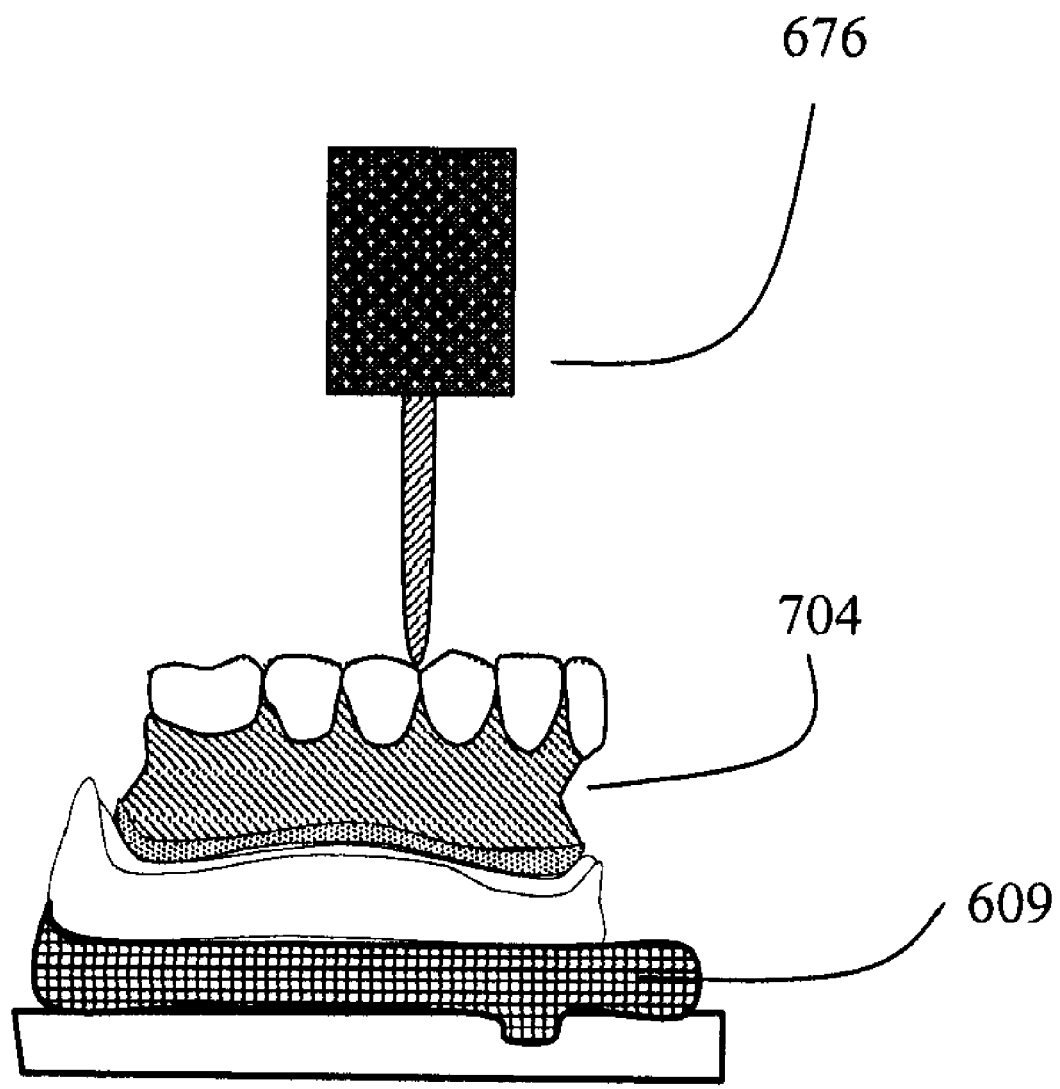
FIG. 32 is an illustration of an exemplary processed upper denture attached to the number controlled mill.

FIG. 32 is a view of the processed upper denture 704 on the mounting plate 609 in the number controlled mill 676. As explained above, the pre-manufactured denture teeth have been cured in the denture base material, and now they may be returned to the mounting plate. Any errors introduced during the processing are corrected by machining, such as by milling, the surfaces of the denture teeth to the shape of the virtual denture. Since the exact orientation of the upper cast is known in relation to the mounting plate and the mill, it is a simple process to attach the processed denture and cast to the mill and cut the biting surfaces to insure they are the same shape as originally designed. This ensures a better fit than traditional methods, where processing errors were not easily detected or repaired.

Figure 33:
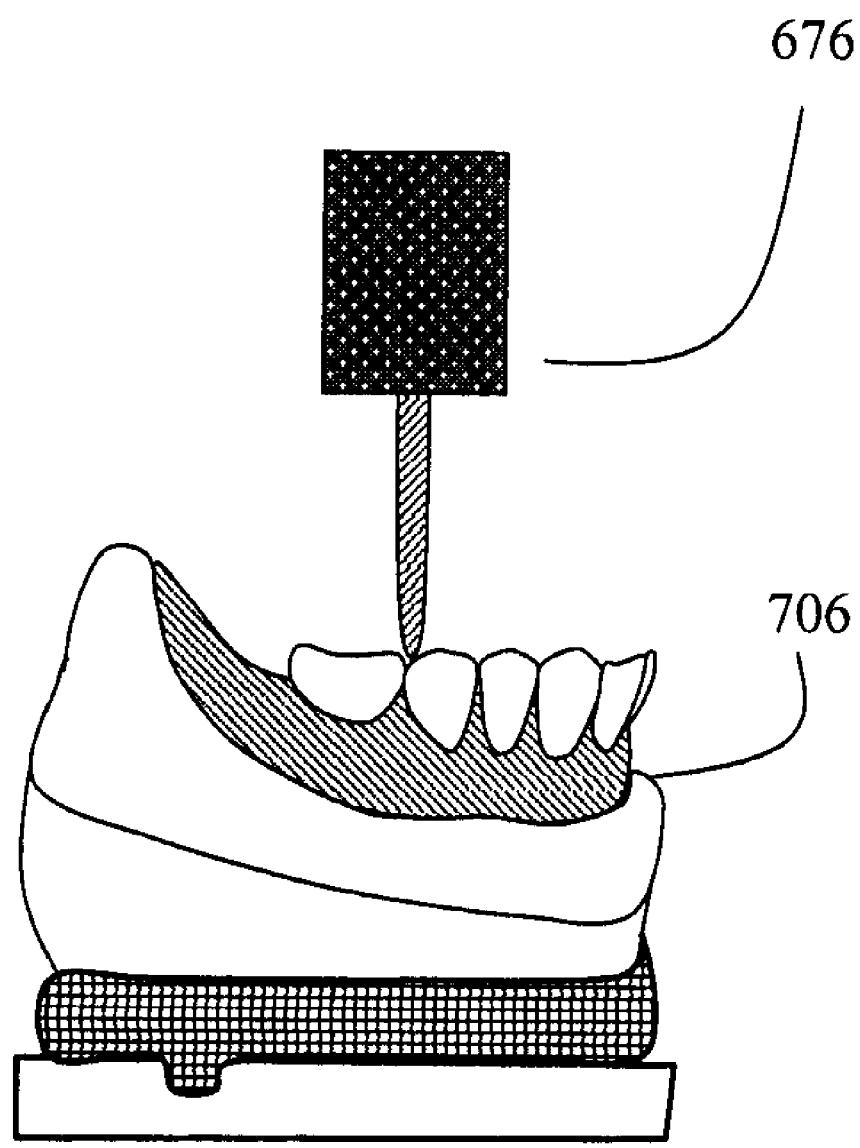
FIG. 33 is an illustration of a view of an exemplary lower processed denture attached to the number controlled mill with the surface of the posterior teeth being milled to the mandibular movement of the patient.

FIG. 33 shows the processed lower denture returned to the mounting plate and being milled, as was the upper, to remove processing errors. In addition, the lower teeth are cut with the mill to have a surface that is in harmony with upper teeth as they move against the lower tooth surfaces. This harmony is accomplished by recording the virtual movements of the upper teeth in centric, lateral and protrusive position and to use Boolean computer operations remove virtual material from the surface of the lower denture teeth and create surfaces that are in harmony with the patient's jaw movement, as discussed above with reference to FIG. 31. The surface of the teeth is saved as a .stl file and translated to numeric code that cuts the surface of the lower denture teeth with a computer controlled mill. This is a simple process using Boolean operations and recording multiple upper jaw positions in relation to the lower.

Figure 39:
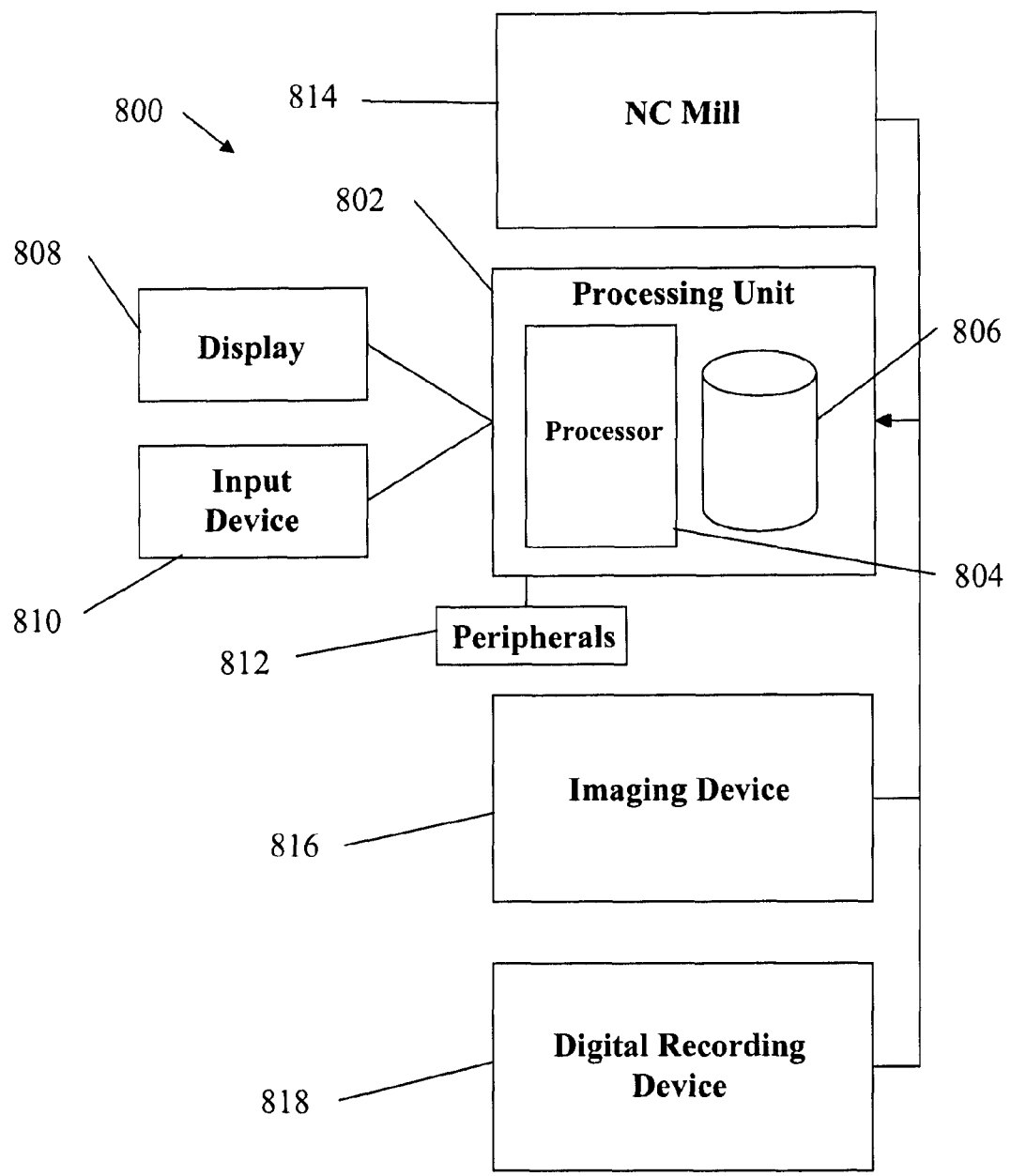
FIG. 39 is a block diagram of an exemplary system usable to accomplish the methods disclosed herein.

An exemplary system for performing the processes and methods described herein is shown in FIG. 39. FIG. 39 includes a computer system 800 including a processing unit 802 containing a processor 804 and a memory 806. An output device, such as a display 808 and input devices 810, such as keyboards, scanners, and others, are in communication with the processing unit 802. Additional peripheral devices 812 also may be present.

The processor 804 may for example be a microprocessor of a known type. The memory 806 may, in some embodiments, collectively represents two or more different types of memory. For example, the memory 506 may include a read only memory (ROM) that stores a program executed by the processor 804, as well as static data for the processor 804. In addition, the memory 806 may include some random access memory (RAM) that is used by the processor 804 to store data that changes dynamically during program execution. The processor 804 and the memory 806 could optionally be implemented as respective portions of a known device that is commonly referred to as a microcontroller. The memory 806 may contain one or more executable programs to carry out the methods contained herein, including joining, separating, storing, and other actions including Boolean actions. In addition, the memory also may include stored image data of a plurality of pre-manufactured teeth that is retrievable using the processor 804 to select one or images. In some exemplary embodiments, the images may be stored on a database accessible only over a network connection, such as a WAN or LAN including the Internet, among other networks. Further, the processing unit 802 may be configured to generate programming code for operating a tool cutting machine, such as an NC mill, as described below.

The system 800 also may include a machining tool, such as an NC mill 814, an imaging device 816, and a digital recorder 818. The NC mill 814 may be any other machining suitable for machining the pre-fabricated teeth, positioning blocks, record bases, wax rims, or other components as described herein. Data from the NC mill 814, the imaging device 816, and the digital recorder 818 may be accessed by the processing unit 802 and used to carry out the processes and methods disclosed. Data may be communicated to or from the processing unit 802 to the NC mill 814, the imaging device 816, and the digital recorder 818 by any known method, including by direct communication, by storing and physically delivering, such as using a removable disc, removable drive, or other removable storage device, over e-mail, or using other known transfer systems over a network, such as a LAN or WAN, including over the Internet or otherwise. Any data received at the processing unit 802 may be stored in the memory 806 for processing and manipulation by the processor 804. In some embodiments, the memory 806 is a storage database separate from the processor 804. Other systems also are contemplated.

Immediate Denture Construction

Frequently patients have teeth that must be removed due to dental decay or periodontal disease. New advances in dental implant treatment make it possible to create artificial teeth attached or supported by dental implants. Immediate dentures are made for these patients and the immediate dentures are made before the natural teeth are removed. The steps of record base construction and wax try-in fitting of the tooth setup is impossible because the patient's natural teeth are still present. In prior art, the dental technician mounted the casts of the patients upper and lower arch in an articulator and then cut the remaining teeth from the cast one at a time and placed artificial denture teeth in position to replace them. This is a time consuming process and unpredictable because the position of the teeth could not be tried in the patient's mouth until the remaining teeth were removed. It was also difficult to determine the shape of the patients face, curve of the lower lip, aesthetic plane of the patient's face and many other types of evaluation that were possible with a conventional wax try-in of the tooth positions in a patient with all their teeth removed. Revealed in this patent is a process that provides for the evaluation of the aesthetic and functional position of the artificial teeth before the teeth are removed. It also makes it possible to position virtual dental implants and to create computer generated drill guides and restorations attached to dental implants even before the teeth have been removed and dental implants placed.

Figure 34:
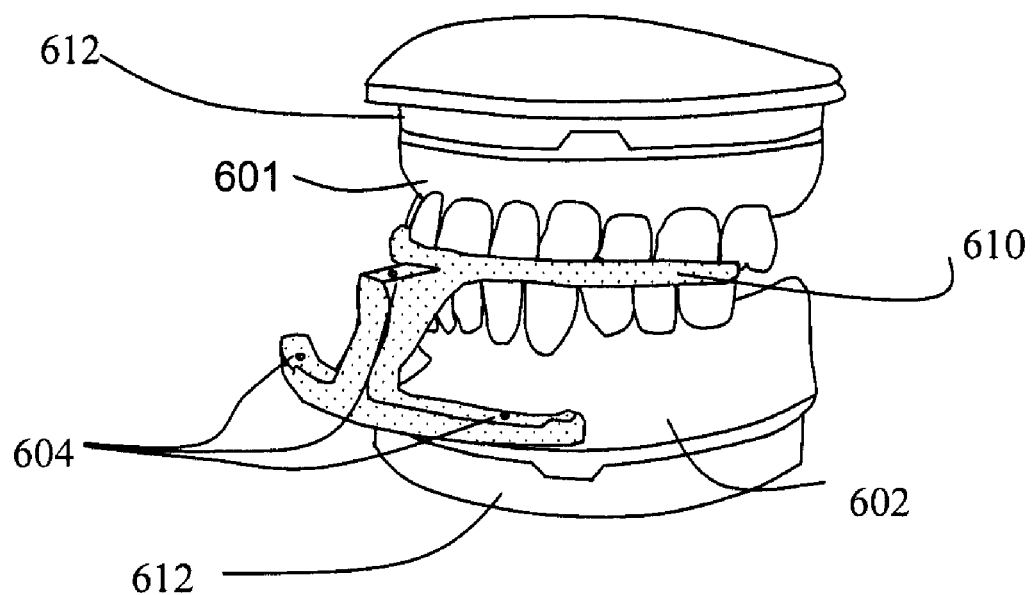
FIG. 34 is an illustration of upper and lower dental casts with teeth in an exemplary CT bite plate.

U.S. patent application Ser. No. 11/674,956, filed Feb. 14, 2007, incorporated by reference, reveals a method of imaging dental casts and the patient in a computed tomography (CT) machine to create a virtual computer model of the patient's teeth and supporting bone and tissue. This process eliminates the radiographic scatter due to dental restorations and replaces the scatter with precise data about the dental casts. FIG. 34 illustrates the upper dental cast 601 and lower dental cast 602 positioned into the CT bite plate 610 to reproduce the precise jaw position made in the CT scan. Three radiographic markers 604 record the orientation of the CT bite plate during the CT scan and allow for creation of a virtual model of the dental casts and scan data from the CT in a precise accurate 3D orientation. Each cast is also joined to a mounting plate that precisely connects to a mounting plate receiver 612. This process can also move virtual image data of the lower jaw and lower teeth to the same orientation made with the centric bite record. FIG. 34 may be substantially the same as CT bite plate 614 described with reference to FIG. 5.

Turning back to FIG. 15, as described above, FIG. 15A illustrates the virtual image of the soft tissue created by volume rendering the pixels in the CT data that are the same grayscale as the soft tissue, this is a well known process in the medial imaging art. It can be seen that many areas of analysis can be made of the face to select the proper size, shape and position of denture teeth to be in harmony with the patients face. FIG. 15B illustrates volume rendering of CT data to create a virtual model of the bones and teeth in the same spatial orientation as the soft tissue of the face. Note that the image data is recorded in relation to the horizontal plane 603 for aesthetic planning.

FIG. 35A illustrates a two dimensional photograph made of the patient smiling. This gives information about the muscles of the mouth, length of the lip and shape of the lips and teeth that are displayed when smiling. FIG. 35B illustrates a 3D rendering of the teeth and bone of the patient from CT data. The form of the teeth is frequently distorted due to radiographic scatter. FIG. 35C illustrates the 3D image of the bone rendered from CT data joined to scan data of the teeth made by scanning the dental casts and orienting them in computer space with the CT bite plate. This gives a very accurate representation of the patient's teeth, occlusion and aesthetic appearance. FIG. 35D is a line drawing of the position of the patient's teeth in relation to the lips when smiling.

Now referring to FIG. 36A is illustrated a 3D virtual model of the patients upper jaw with the teeth removed. This is accomplished by creating .stl files of the teeth separately from the .stl file of the upper jaw and then using a Boolean operation to remove the teeth from the upper jaw computer model. FIG. 36B illustrates the placement of virtual denture teeth to replace the teeth that will be extracted. This is an easy process because the teeth can be turned on or off to note their position. Unlike previous art, the natural teeth do not have to be cut from a dental cast to have space for the replacement denture tooth. The computer can easily store the position and form of the denture teeth as well as the teeth that are to be removed. FIG. 36C illustrates the aesthetic appearance of the denture teeth placed in the space created when the patient smiles. This will be a very accurate representation of the appearance of the patient when the immediate denture is inserted.

Figure 37:
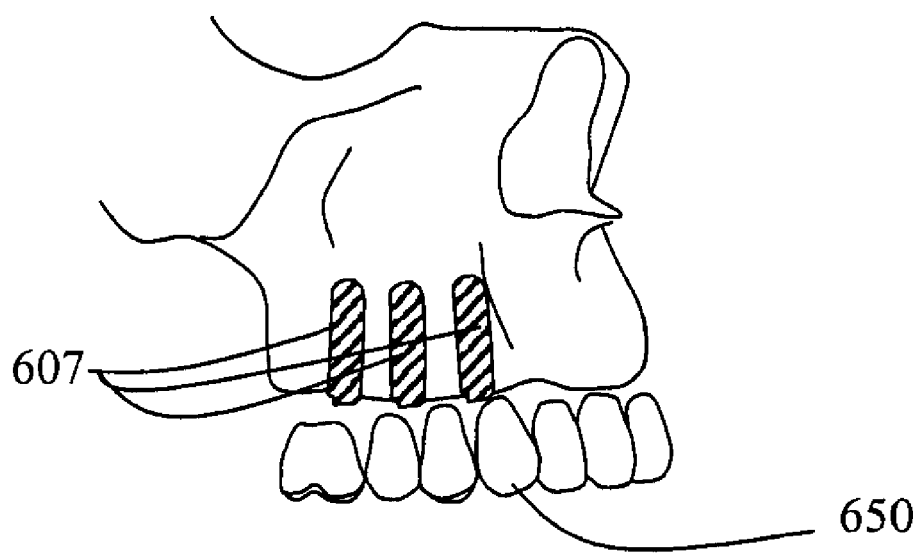
FIG. 37 is an illustration of an exemplary upper virtual jaw model with virtual implants placed in the supporting bone. An exemplary position of the virtual denture teeth is also illustrated.

FIG. 37 illustrates the placement of virtual dental implants 607 into the virtual model of the patient. The position the implants can be planned in relation to the virtual denture teeth 650 before any surgery. This makes it possible to create drill guides to help in the placement of dental implants using NC milling or layered manufacturing of the guides. It also makes it possible to mill bore holes in the immediate denture in the same location and angle as was used to place the implants with the drill guide. Finally, temporary abutment cylinders can be placed in the bore holes at the time of surgery to create an immediate load type prosthesis.

FIG. 38A illustrates the process of milling the dental cast to remove plaster teeth using a number controlled mill. The virtual computer model creates code that cuts the cast (FIG. 38B) similar to the way the patient will be after their teeth are removed. This cast can then be used to process the denture teeth to it as described in this patent (FIG. 38C).

In one exemplary aspect the present disclosure is directed to a method of manufacturing a dental prosthetic. The method may include arranging a first virtual tooth image relative to a second virtual tooth image on a virtual denture set and locating a first actual prosthetic tooth relative to a second actual prosthetic tooth in a manner corresponding to the arranged first and second virtual images. The method also may include performing at least one Boolean operation to remove a portion of the first virtual tooth image and the second virtual tooth image and machining the first actual prosthetic tooth and the second actual prosthetic tooth to remove a portion of material corresponding to that removed by the Boolean operation performed on the first and second virtual tooth images.

In some exemplary aspects the method may include generating a virtual positioning block having indentations shaped to fit the first and second virtual teeth images and manufacturing an actual positioning block corresponding to the virtual positioning block. In some exemplary aspects the method may include placing the first and second actual prosthetic teeth in the indentations in the actual positioning block and wherein machining the first and second prosthetic teeth is performed with the first and second actual prosthetic teeth in the indentations. In some exemplary aspects generating a virtual positioning block includes creating the virtual block over the first and second virtual teeth images and removing the shape of the first and second virtual teeth from the virtual block. In some exemplary aspects the method may include generating a virtual image of a dental cast of a portion of a patient's inner mouth. In some exemplary aspects the method may include creating one of a record base and a wax rim based on the virtual image of the dental cast. In some exemplary aspects the method may include one of: machining the one of the record base and the wax rim; and digital layer manufacturing the one of the record base and the wax rim. In some exemplary aspects machining the first and second actual prosthetic teeth includes generating programming data for operating a tool cutting machine to cut shapes corresponding to the virtual material removed by the Boolean operation; and transferring the programming data to the tool cutting machine. In some exemplary aspects, the tool cutting machine is an NC mill. In some exemplary aspects the first and second virtual tooth images are computer generated 3-D models. In some exemplary aspects the method may include retrieving the first and second virtual tooth images from a plurality of virtual tooth images corresponding to pre-manufactured dental teeth. In some exemplary aspects the method may include securing the machined first and second actual prosthetic teeth in position relative to each other with a securing material. In some exemplary aspects the securing material is wax. In some exemplary aspects the method may include receiving information relating to alignment of the first and second actual prosthetic teeth relative to a patient's opposing dental elements; and generating virtual images of the patient's opposing dental elements; recording the information relating to the alignment to determine virtual interferences between the first virtual tooth image and opposing virtual dental elements; and removing at least a portion of the virtual interferences using Boolean operations. In some exemplary aspects the method may include machining the first actual prosthetic tooth to remove actual interferences corresponding to the removed virtual interferences. In some exemplary aspects, the method may include scanning the first and the second actual prosthetic teeth to generate the first virtual tooth image and second virtual tooth image, respectively.

In another exemplary aspect, the present disclosure is directed to method of manufacturing a dental prosthetic. The method may include preparing a first try-in prosthetic having actual prosthetic teeth for a patient, the first try-in prosthetic being one of an upper dental prosthetic and a lower dental prosthetic and receiving information relating to alignment of the first try-in prosthetic within a patient's mouth relative to dental elements of the opposing arch. The method also may include recording the information relating to the alignment as virtual images and determining virtual interferences between the first try-in prosthetic and the dental elements of the opposing arch. It also may include machining the actual prosthetic teeth to remove interferences.

In some exemplary aspects the first try-in is formed in wax, and further including: removing the wax from the actual prosthetic teeth; and fixing the actual prosthetic teeth relative to each other with a binding material. In some exemplary aspects the method may include machining the fixed prosthetic teeth to remove processing error introduced when performing one of said removing the wax and fixing the actual prosthetic teeth. In some exemplary aspects machining the fixed actual prosthetic teeth includes machining the teeth to match a machined profile of the teeth in the first try-in prosthetic. In some exemplary aspects the information relating to the alignment includes recording one of centric and protrusive positions of the first try-in prosthetic. In some exemplary aspects the dental elements of the opposing arch are one of natural or prosthetic teeth. In some exemplary aspects the method may include removing virtual interferences from the virtual images using Boolean operations. In some exemplary aspects machining the actual prosthetic teeth includes: generating programming data for operating a tool cutting machine to cut shapes corresponding to the virtual interferences removed by the Boolean operation; and transferring the programming data to the tool cutting machine. In some exemplary aspects the tool cutting machine is an NC mill.

In another exemplary aspect, this disclosure is directed to a method of manufacturing a dental prosthetic. The method may include generating a virtual dental cast corresponding to an actual dental cast of a portion of a patient's inner mouth and generating a virtual record base and a virtual rim. It also may include virtually locating a virtual tooth image at desired location relative to at least one of the virtual dental cast, the virtual rim, and the virtual record base and locating an actual prosthetic tooth corresponding to the virtual tooth image on a corresponding location on the actual dental cast.

In some exemplary aspects the method may include generating a virtual dental cast includes scanning the actual dental cast. In some exemplary aspects the method may include creating an actual record base and an actual rim using one of an NC mill and a digital layer manufacturing system, including: generating programming data for operating the one of an NC mill and a digital layer manufacturing system, and transferring the programming data to the one of an NC mill and a digital layer manufacturing system. In some exemplary aspects the method may include selecting the virtual tooth image from a plurality of stored virtual tooth images, each of the plurality of virtual tooth images corresponding to an actual pre-manufactured tooth. In some exemplary aspects the method may include creating a virtual positioning block overlapping the virtual tooth image and removing the virtual tooth image from the virtual positioning block to generate a virtual indentation in the virtual positioning block matching the virtual tooth image. It also may include machining an actual positioning block to have an actual indentation corresponding to the virtual indentation. In some exemplary aspects the method may include placing the actual prosthetic tooth into the indentation in the actual positioning block and machining the actual prosthetic tooth to cooperatively fit the actual dental cast.

In another exemplary aspect, this disclosure is directed to a method of manufacturing a dental prosthetic. The method may include generating a virtual image of a rim configured to fit an alveolar ridge of a patient and selecting a virtual tooth image of at least one tooth from a memory storing a plurality of virtual tooth images, the virtual tooth image corresponding to an actual prosthetic tooth. The virtual tooth image may be arranged at a desired location on the image of the rim and a Boolean operation may be performed to remove a portion of the virtual tooth image. A virtual positioning block overlapping the virtual tooth image may be created. The method also may include removing the virtual tooth image from the virtual positioning block to generate a virtual indentation in the virtual positioning block matching the virtual tooth and machining an actual positioning block to have an actual indentation corresponding to the virtual indentation. It also may include placing the actual prosthetic tooth into the indentation in the actual positioning block and generating first programming data for operating a tool cutting machine to cut a shape corresponding to the portion of the virtual tooth image removed by the Boolean operation, transferring the first programming data to the tool cutting machine, and machining the actual prosthetic tooth to remove material corresponding to the portion removed from the virtual tooth image by the Boolean operation. It also may include preparing a first try-in prosthetic including the actual prosthetic tooth for the patient, the first try-in prosthetic being one of an upper dental prosthetic and a lower dental prosthetic. The method further may include receiving information relating to alignment of the first try-in prosthetic within the patient's mouth, recording the information relating to the alignment as virtual images, and determining virtual interferences between the first try-in prosthetic and patient's opposing dental elements. At least a part of the virtual interferences in the virtual image may be removed by a Boolean operation. Second programming data may be generated for operating a tool cutting machine to cut shapes corresponding to the virtual interferences removed by the Boolean operation. The second programming data may be transferred to the tool cutting machine, and the actual prosthetic tooth may be machined to match the virtual tooth image and remove the real interferences.

In yet another exemplary aspect, the present disclosure is directed to a method of manufacturing an immediate denture. The method may include generating a virtual image of a dental cast, the virtual image including the teeth of the dental cast. It also may include virtually removing the teeth from the virtual image to create a virtual alveolar ridge and selecting a virtual tooth image from a memory storing a plurality of tooth images, the virtual tooth image corresponding to an actual prosthetic tooth. The method also may include arranging the virtual tooth image at a desired location on the virtual image of the virtual alveolar ridge and may include using a Boolean operation to remove a portion of the virtual tooth image. Programming data may be generated for operating a tool cutting machine to cut shapes corresponding to the portion of the virtual tooth image removed by the Boolean operation. The programming data may be transferred to the tool cutting machine, and the actual prosthetic tooth may be machined to remove material to match the virtual tooth image.

In some exemplary aspects, generating a virtual image of the dental cast includes scanning the dental cast with a CT scanner and a bite plate. In some exemplary aspects the method may include generating a 3D virtual model of the patient's head based on a scan with a CT scanner. In some exemplary aspects the method may include generating an image of the patient's head showing soft tissue and showing the virtual tooth image in place on the patient's head image.

In yet another exemplary aspect, the present disclosure is directed to a method of treating a dental patient. The method may include scanning the patient's head with a CT scanner to generate a virtual head image of the patient's head, removing the patients virtual teeth from the virtual head image, and selecting a virtual tooth image from a memory storing a plurality of tooth images, the virtual tooth image corresponding to an actual prosthetic tooth. The method also may include arranging the virtual tooth image at a desired location on the virtual head image and displaying the virtual tooth image in the virtual head image.

In some exemplary aspects the method may include scanning a dental cast of the patient's teeth to generate a virtual dental cast; and placing the virtual dental cast on the virtual head image. In some exemplary aspects, displaying includes showing the tooth image to the patient.

In some exemplary aspects displaying the virtual tooth image in the virtual head image includes displaying the soft tissue of the virtual head image. In some exemplary aspects the method may include creating a patient treatment plan considering the aesthetics of the virtual tooth image in the virtual head image. In some exemplary aspects the method may include placing virtual implants into the virtual head image of the patient. In some exemplary aspects the method may include creating a drill guide based upon the virtual head image.

In one exemplary aspect, this disclosure is directed toward a system for manufacturing a dental prosthetic. The system may include means for arranging a first virtual tooth image relative to a second virtual tooth image on a virtual denture set and may also include means for locating a first actual prosthetic tooth relative to a second actual prosthetic tooth in a manner corresponding to the arranged first and second virtual images. The method further may include means for performing at least one Boolean operation to remove a portion of the first virtual tooth image and the second virtual tooth image, and means for machining the first actual prosthetic tooth and the second actual prosthetic tooth to remove a portion correspond to material removed by the Boolean operation performed on the first and second virtual tooth images.

In some exemplary aspects, the system may include means for generating a virtual positioning block having indentations shaped to fit the first and second virtual teeth images, and means for manufacturing an actual positioning block corresponding to the virtual positioning block. In some exemplary aspects, the system may include means for placing the first and second actual prosthetic teeth in the indentations in the actual positioning block and wherein the means for machining the first and second prosthetic teeth includes machining with the first and second actual prosthetic teeth in the indentations. In some exemplary aspects, the means for generating a virtual positioning block includes means for creating the virtual block over the first and second virtual teeth images and means for removing the shape of the first and second virtual teeth from the virtual block. In some exemplary aspects, the system may include means for generating a virtual image of a dental cast of a portion of a patient's inner mouth. In some exemplary aspects, the system may include means for creating one of a record base and a wax rim based on the virtual image of the dental cast. In some exemplary aspects, the system may include one of: means for machining the one of the record base and the wax rim; and means for digital layer manufacturing the one of the record base and the wax rim. In some exemplary aspects, the means for machining the first and second actual prosthetic teeth includes: means for generating programming data for operating a tool cutting machine to cut shapes corresponding to the virtual material removed by the Boolean operation; and means for transferring the programming data to the tool cutting machine. In some exemplary aspects, the tool cutting machine is an NC mill. In some exemplary aspects, the first and second virtual tooth images are computer generated 3-D models. In some exemplary aspects, the system may include means for retrieving the first and second virtual tooth images from a plurality of virtual tooth images corresponding to pre-manufactured dental teeth. In some exemplary aspects, the system may include means for securing the machined first and second actual prosthetic teeth in position relative to each other with a securing material. In some exemplary aspects, the securing material is wax. In some exemplary aspects, the system may include means for receiving information relating to alignment of the first and second actual prosthetic teeth relative to a patient's opposing dental elements, may include means for generating virtual images of the patient's opposing dental elements, may include means for recording the information relating to the alignment to determine virtual interferences between the first virtual tooth image and opposing virtual dental elements, and means for removing at least a portion of the virtual interferences using Boolean operations. In some exemplary aspects, the system may include means for machining the first actual prosthetic tooth to remove actual interferences corresponding to the removed virtual interferences. In some exemplary aspects, the system may include means for scanning the first and the second actual prosthetic teeth to generate the first virtual tooth image and second virtual tooth image, respectively.

In yet another exemplary aspect, this disclosure is directed to a system of manufacturing a dental prosthetic. The system may include means for preparing a first try-in prosthetic having actual prosthetic teeth for a patient, the first try-in prosthetic being one of an upper dental prosthetic and a lower dental prosthetic, and may include means for receiving information relating to alignment of the first try-in prosthetic within a patient's mouth relative to dental elements of the opposing arch. The system further may include means for recording the information relating to the alignment as virtual images, means for determining virtual interferences between the first try-in prosthetic and the dental elements of the opposing arch, and means for machining the actual prosthetic teeth to remove interferences.

In some exemplary aspects, the first try-in is formed in wax, and the system further includes means for removing the wax from the actual prosthetic teeth, and means for fixing the actual prosthetic teeth relative to each other with a binding material. In some exemplary aspects, the system may include means for machining the fixed prosthetic teeth to remove processing error introduced when performing one of said removing the wax and fixing the actual prosthetic teeth. In some exemplary aspects, the means for machining the fixed actual prosthetic teeth includes means for machining the teeth to match a machined profile of the teeth in the first try-in prosthetic. In some exemplary aspects, the information relating to the alignment includes one of centric and protrusive positions of the first try-in prosthetic. In some exemplary aspects, the dental elements of the opposing arch are one of natural or prosthetic teeth. In some exemplary aspects, the system may include means for removing virtual interferences from the virtual images using Boolean operations. In some exemplary aspects, the means for machining the actual prosthetic teeth includes: means for generating programming data for operating a tool cutting machine to cut shapes corresponding to the virtual interferences removed by the Boolean operation; and means for transferring the programming data to the tool cutting machine. In some exemplary aspects, the tool cutting machine is an NC mill.

In another exemplary aspect, the present disclosure is directed to a system of manufacturing a dental prosthetic. The system may include means for generating a virtual dental cast corresponding to an actual dental cast of a portion of a patient's inner mouth, means for generating a virtual record base and a virtual rim, means for virtually locating a virtual tooth image at desired location relative to at least one of the virtual dental cast, the virtual rim, and the virtual record base, and means for locating an actual prosthetic tooth corresponding to the virtual tooth image on a corresponding location on the actual dental cast.

In some exemplary aspects, the means for generating a virtual dental cast includes scanning the actual dental cast. In some exemplary aspects, the system may include means for creating an actual record base and an actual rim using one of an NC mill and a digital layer manufacturing system, including: means for generating programming data for operating the one of an NC mill and a digital layer manufacturing system, and means for transferring the programming data to the one of an NC mill and a digital layer manufacturing system. In some exemplary aspects, the system may include means for selecting the virtual tooth image from a plurality of stored virtual tooth images, each of the plurality of virtual tooth images corresponding to an actual pre-manufactured tooth. In some exemplary aspects, the system may include means for creating a virtual positioning block overlapping the virtual tooth image; means for removing the virtual tooth image from the virtual positioning block to generate a virtual indentation in the virtual positioning block matching the virtual tooth image; and means for machining an actual positioning block to have an actual indentation corresponding to the virtual indentation. In some exemplary aspects, the system may include means for placing the actual prosthetic tooth into the indentation in the actual positioning block; and means for machining the actual prosthetic tooth to cooperatively fit the actual dental cast.

In yet another exemplary aspect, the present disclosure is directed to a system of manufacturing an immediate denture. The system may include generating a virtual image of a dental cast, the virtual image including the teeth of the dental cast. The system also may include means for virtually removing the teeth from the virtual image to create a virtual alveolar ridge and means for selecting a virtual tooth image from a memory storing a plurality of tooth images, the virtual tooth image corresponding to an actual prosthetic tooth; Additionally, the system may include means for arranging the virtual tooth image at a desired location on the virtual image of the virtual alveolar ridge, means for using a Boolean operation to remove a portion of the virtual tooth image, and means for generating programming data for operating a tool cutting machine to cut shapes corresponding to the portion of the virtual tooth image removed by the Boolean operation. The system may further include means for transferring the programming data to the tool cutting machine; and means for machining the actual prosthetic tooth to remove material to match the virtual tooth image.

In some exemplary aspects, the means for generating a virtual image of the dental cast includes means for scanning the dental cast with a CT scanner and a bite plate. In some exemplary aspects, the system may include means for generating a 3D virtual model of the patient's head based on a scan with a CT scanner. In some exemplary aspects, the system may include means for generating an image of the patient's head showing soft tissue and showing the virtual tooth image in place on the patient's head image.

In yet another exemplary aspect, the present disclosure is directed to a system of treating a dental patient. The system may include means for scanning the patient's head with a CT scanner to generate a virtual head image of the patient's head and may include means for removing the patients virtual teeth from the virtual head image. Further, the system may include means for selecting a virtual tooth image from a memory storing a plurality of tooth images, the virtual tooth image corresponding to an actual prosthetic tooth, means for arranging the virtual tooth image at a desired location on the virtual head image, and means for displaying the virtual tooth image in the virtual head image.

In some exemplary aspects, the system may include means for scanning a dental cast of the patient's teeth to generate a virtual dental cast; and means for placing the virtual dental cast on the virtual head image. In some exemplary aspects, the means for displaying includes showing the tooth image to the patient. In some exemplary aspects, the means for displaying the virtual tooth image in the virtual head image includes means for displaying the soft tissue of the virtual head image. In some exemplary aspects, the system may include means for creating a patient treatment plan considering the aesthetics of the virtual tooth image in the virtual head image. In some exemplary aspects, the system may include means for placing virtual implants into the virtual head image of the patient. In some exemplary aspects, the system may include means for creating a drill guide based upon the virtual head image.

Although several selected embodiments have been illustrated and described in detail, it will be understood that they are exemplary, and that a variety of substitutions and alterations are possible without departing from the spirit and scope of the present invention, as defined by the following claims. Further, it is contemplated that features disclosed in any one embodiment, system, or method may be used on any other embodiment, system, or method.

I claim:

1. A method of manufacturing a dental prosthetic, comprising:
    arranging a first virtual tooth image relative to a second virtual tooth image on a virtual denture set;
    said first virtual tooth image and said second virtual tooth image respectively representative of a first actual prosthetic tooth and a second actual prosthetic tooth;
    performing at least one Boolean operation to remove a virtual portion of the first virtual tooth image and the second virtual tooth image;
    machining the first actual prosthetic tooth and the second actual prosthetic tooth to remove an actual portion of prosthetic tooth material corresponding to said virtual portion removed by the at least one Boolean operation performed on the first and second virtual tooth images;
    generating a virtual positioning block having indentations shaped to fit the first and second virtual teeth images; and
    manufacturing an actual positioning block corresponding to the virtual positioning block.

2. The method of claim 1, including placing the first and second actual prosthetic teeth in the indentations in the actual positioning block and wherein machining the first and second prosthetic teeth is performed with the first and second actual prosthetic teeth in the indentations.

3. The method of claim 1, wherein the generating a virtual positioning block includes creating the virtual block over the first and second virtual teeth images and removing the shape of the first and second virtual teeth from the virtual block.

4. The method of claim 1, including generating a virtual image of a dental cast of a portion of a patient's inner mouth.

5. The method of claim 4, including creating one of a record base and a wax rim based on the virtual image of the dental cast.

6. The method of claim 1, wherein machining the first and second actual prosthetic teeth includes:

generating programming, data for operating a tool cutting machine to cut shapes corresponding to the virtual material removed by the Boolean operation; and transferring the programming data to the tool cutting machine.

7. The method of claim 1, wherein the first and second virtual tooth images are computer generated 3-D models.

8. The method of claim 1, comprising:

receiving information relating to alignment of the first and second actual prosthetic teeth relative to a patient's opposing dental elements; and generating virtual images of the patient's opposing dental elements;

recording the information relating to the alignment to determine virtual interferences between the first virtual tooth image and opposing virtual dental elements; and removing at least a portion of the virtual interferences using Boolean operations.

9. The method of claim 1, including scanning the first and the second actual prosthetic teeth to generate the first virtual tooth image and second virtual tooth image, respectively.

10. A method of manufacturing a dental prosthetic, comprising:

arranging a first virtual tooth image relative to a second virtual tooth image on a virtual denture set;

said first virtual tooth image and said second virtual tooth image respectively representative of a first actual prosthetic tooth and a second actual prosthetic tooth;

performing at least one Boolean operation to remove a virtual portion of the first virtual tooth image and the second virtual tooth image;

machining the first actual prosthetic tooth and the second actual prosthetic tooth to remove an actual portion of prosthetic tooth material corresponding to said virtual portion removed by the at least one Boolean operation performed on the first and second virtual tooth images;

generating a virtual image of a dental cast of a portion of a patient's inner mouth;

creating one of a record base and a wax rim based on the virtual image of the dental cast; and one of:
    machining the one of the record base and the wax rim; and
    digital layer manufacturing the one of the record base and the wax rim.

* * * * *